United States Patent

Diffendall et al.

[11] Patent Number: 5,962,746
[45] Date of Patent: Oct. 5, 1999

[54] PROCESS FOR PREPARING PEROXIDES

[75] Inventors: George Francis Diffendall; Thomas William Harding, both of Wilmington; Joseph Norman Hockman, Hockessin; Carl George Krespan, Wilmington, all of Del.; Matthew John Targett, Greenville, N.C.; Robert Clayton Wheland, Wilmington, Del.

[73] Assignee: E. I. du Pont de Nemours and Company, Wilmington, Del.

[21] Appl. No.: 09/128,506

[22] Filed: Aug. 4, 1998

Related U.S. Application Data

[62] Division of application No. 08/703,232, Aug. 26, 1996.
[51] Int. Cl.[6] .................................................. C07C 409/00
[52] U.S. Cl. ............................................. 568/560; 568/566
[58] Field of Search ....................... 568/560, 566; 560/180, 184

[56] References Cited

U.S. PATENT DOCUMENTS

| | | |
|---|---|---|
| 1,614,037 | 1/1927 | McKee . |
| 1,718,609 | 6/1929 | Stoddard . |
| 2,559,630 | 7/1951 | Bullitt, Jr. ................................ 260/610 |
| 2,580,373 | 5/1951 | Zimmerman ............................ 260/610 |
| 2,792,423 | 5/1957 | Young . |
| 3,377,373 | 4/1968 | Lederer et al. ......................... 260/463 |
| 3,461,155 | 8/1969 | Rice ........................................ 260/479 |
| 4,075,236 | 2/1978 | Wagle . |
| 4,654,444 | 3/1987 | Oka et al. ............................... 568/560 |
| 4,663,407 | 5/1987 | Oka et al. ............................... 526/209 |
| 5,021,516 | 6/1991 | Wheland . |
| 5,256,825 | 10/1993 | Fukaya et al. ......................... 564/510 |
| B1 4,075,236 | 9/1985 | Wagle . |

FOREIGN PATENT DOCUMENTS

| | | | |
|---|---|---|---|
| 1330351 | 6/1994 | Canada .......................... C07C 19/08 |
| 405 396 | 1/1991 | European Pat. Off. ...... C07C 409/34 |
| 606 492 | 7/1994 | European Pat. Off. ...... C08F 214/26 |
| WO 91/00272 | 1/1991 | WIPO ......................... C07C 409/32 |

OTHER PUBLICATIONS

Malinovskii, M.S. et al., Haloperacetic Acids, *Zh. Org. Khim.*, 7(4), 673–677, Apr. 1971.

Foutch et al., Reactors in Process Engineering, *Encyclopedia of Physical Science and Technology*, 12, 56–60, 1987.

Chengxue, Zhao et al., Thermal Decomposition of Some Perfluoro– and Polyfluorodiacyl Peroxides, *J. Org. Chem.*, 47, 2009–2013, 1982.

Chemical Abstracts, vol. 119, No. 13, Sep. 27, 1993, Abstract No. 138748.

*Primary Examiner*—Gary Geist
*Assistant Examiner*—Jean F Vollano

[57] ABSTRACT

A process for the faster manufacturing of hydrocarbon, fluorocarbon and chlorocarbon acyl peroxides is disclosed wherein a hydroxide, a peroxide and an acyl halide are reacted under continuous vigorous agitation conditions so as to bring the reaction to substantial completion is less than one minute.

39 Claims, 3 Drawing Sheets

PROCESS FOR PREPARING PEROXIDES

This case is a division of Ser. No. 08/703,232 filed on Aug. 26, 1996.

FIELD OF THE INVENTION

The present invention relates to a near instantaneous process for the manufacture of hydrocarbon, fluorocarbon and chlorocarbon acyl peroxides. This process uses simple equipment and is particularly safe for the thermally least stable peroxides. Acyl peroxides are useful as initiators for vinyl polymerization and in organic synthesis.

TECHNICAL BACKGROUND OF THE INVENTION

Perfluoroacyl peroxides are commonly made by stirring aqueous hydroxide and hydrogen peroxide (or metal peroxides such as $Na_2O_2$) with an acyl chloride or fluoride dissolved in an organic solvent. Reaction times typically range from about 1 minute to about 60 minutes.

Perfluoroacyl peroxides are generally thought of as too hydrolytically unstable to be useful as initiators in the presence of water. Thus, as the intensity of stiring or emulsification is increased in the synthesis of a perfluoroacyl peroxide, a point may be reached at which peroxide yields decrease as a result of competing hydrolysis reactions. Ultrasonics exposure, in particular, is known to have an accelerating effect on the hydrolysis of organic compounds.

U.S. Pat. No. 4,075,236 passes acid chloride, hydroperoxide, and aqueous alkali metal hydroxide through a series of two mechanically stirred reaction vessels to produce peroxyesters of the formula $R_y$-[(C=O)OO]$_n$R'. Structures R and R' are left quite general in the claims but it should be noted that all specific examples contain only carbon and hydrogen. Although it appears that this patent claims accelerated reaction rates, the examples are written so that exact reaction times are not mentioned. (Assuming, however, that the 10 gallon reactor size discussed in connection with impeller design, at column 4 line 20, applies to both reactors then the reaction times in the experimental examples would be about 4 minutes).

DD 128663 passes acid halides, hydroperoxide, and aqueous alkali through a series of reactors or possibly a single cascade reactor with intense mixing. This produces peroxyesters of the formula R(C=O)OOR', where the R and R' groups are again exemplified by compounds containing just carbon and hydrogen. Short reaction times of 0.5 to 15 minutes are achieved by using elevated reaction temperatures (40 to 95° C.) in conjunction with a series of vessels to control the heat of reaction.

In U.S. Pat. No. 5,021,516, in which HFPO oligomerperoxides were made from HFPO oligomer acid fluorides, carbonates, and 30% hydrogen peroxide, reaction times were 10 minutes to 7 hours.

SUMMARY OF THE INVENTION

The present invention relates to a process for making peroxides, peroxy-dicarbonates, peroxyesters and peroxyacids by subjecting the reactants to vigorous agitation.

One embodiment is a continuous process for producing perfluoroacyl peroxides comprising the steps of reacting an acyl halide with an aqueous hydroxide mixed with a peroxide selected from the group consisting of hydrogen peroxide and alkyl hydroperoxide wherein the improvement consists of combining specific reactor configurations with specific methods of vigorous agitiation so as to generate a good yield of peroxide product in less than one minute, preferably less than thirty seconds. An aqueous metal peroxide could also be used as a reactant with acyl halide in the process.

In a preferred embodiment of this continuous process, reaction with continuous agitation starts in an agitation (reaction) vessel and continues, with agitation, in transfer lines. Decreasing the accumulation of peroxide in the agitation vessel reduces the threat of explosion and the accumulation of toxic products. Recent tragedies such as the methyl isocyanate disaster in Bhopal, India have suggested that it is desirable to run hazardous reactions partially in the reaction vessel and partially in the transfer lines so as to decrease the accumulation of hazardous substances. In such continuous processes the dimensions of transfer lines are important and should be set up so as to continuously mix the aqueous and organic phases, as described below. In a preferred embodiment at least 10% of peroxide formation occurs in the transfer line.

The process can also be carried on in a similar manner with a batch process by subjecting the batch process to vigorous agitiation. The batch process achieves significantly shorter reaction times in comparison to the prior art. The batch process is particularly useful for the preparation of small lab-scale quantities.

The batch process comprises contacting an acyl halide with either a metal peroxide or with an aqueous hydroxide mixed with a peroxide selected from the group consisting of hydrogen peroxide and an an alkyl hydroperoxide while continuously agitating the reactants, using vigorous agitation means, until substantial completion of the reaction. The reaction is substantially complete in less than one minute.

Jet, static, and ultrasonic agitators are preferred for the continuous process and ultrasonic agitators are preferred for the batch process. Reaction times for completion of the processes are preferably about 0.01 seconds to about 30 seconds.

DETAILED DESCRIPTION OF THE DRAWINGS

Figure 1:
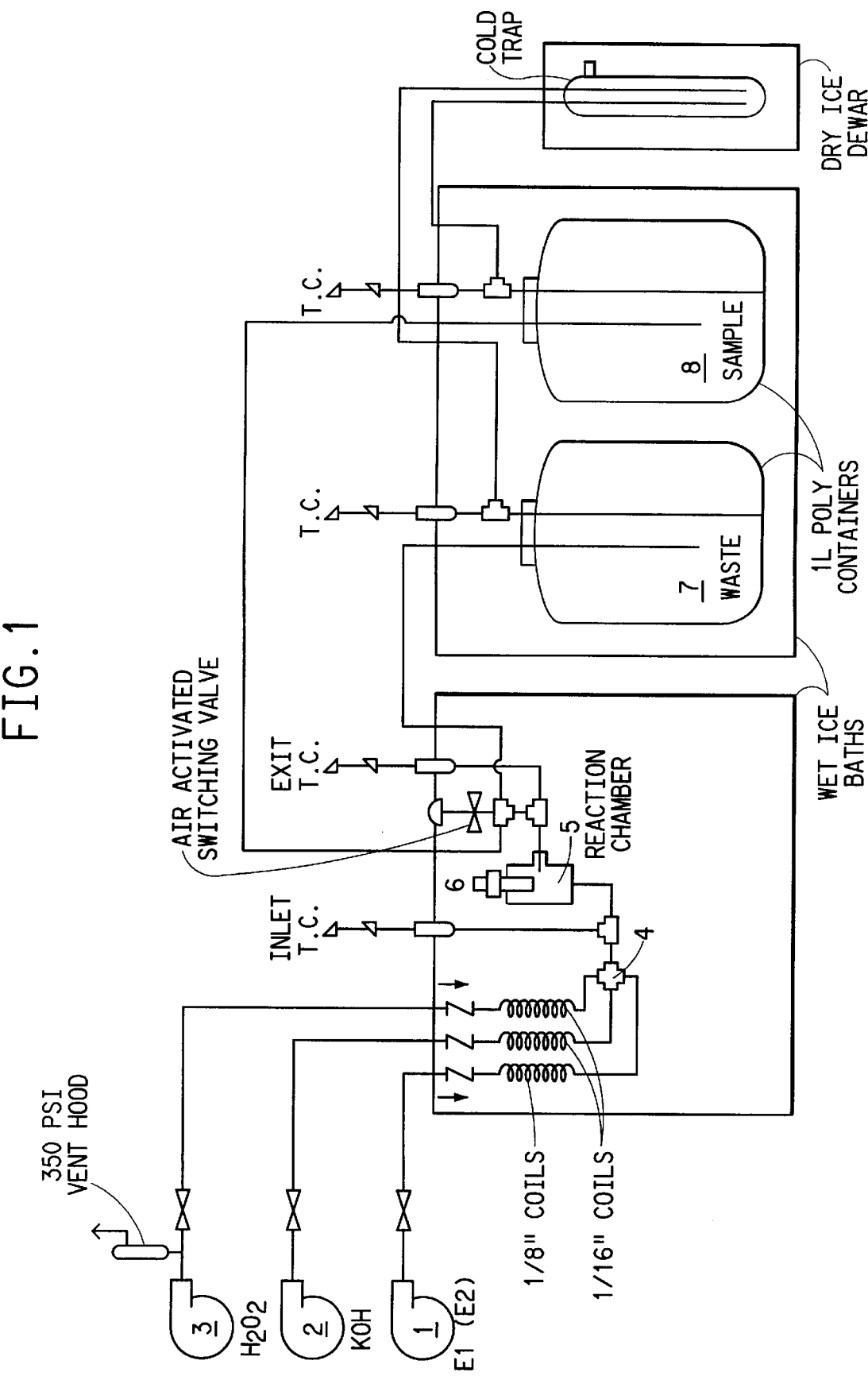
FIG. 1 is a schematic description of a flow reaction system for the continuous ultrasonic embodiment of the process.

In FIG. 1, syringe pump (3) is loaded with aqueous peroxide and syringe pump (2) is loaded with aqueous hydroxide. Syringe pump (1) is loaded with acyl halide, preferably dissolved in an organic solvent such as Freon E2. The streams from the three pumps (1), (2) and (3) are optionally chilled by immersion in wet ice and joined into a single stream at fitting (4). Immediately after exiting fitting (4) the liquid stream is run into reactor cavity (5) which can also be chilled with ice. Ultrasonic horn (6) provides intense mixing in the reactor cavity. The reactor is run for several minutes to flush out the lines. Waste flows into waste container (7). The reactor stream is then diverted to sample poly container (8) where effluent is collected for product analysis.

DETAILED DESCRIPTION OF THE INVENTION

The reaction can be carried out either in a batch process or continuous process.

In a batch process the desirable and surprising result is the reduction in reaction time. The reactants in the batch reactor are contacted simultaneously and continuously agitated. The reaction occurs in less than one minuate, preferably 0.01 to about 30 seconds. The reaction as practiced, for example, in Example 23, results in an unexpectedly stable aqueous dispersion of peroxide. Such a dispersion, if promptly used as an initiator for polymerization, can result in an aqueous dispersion of polymer which may be useful in coating applications.

Figure 2:
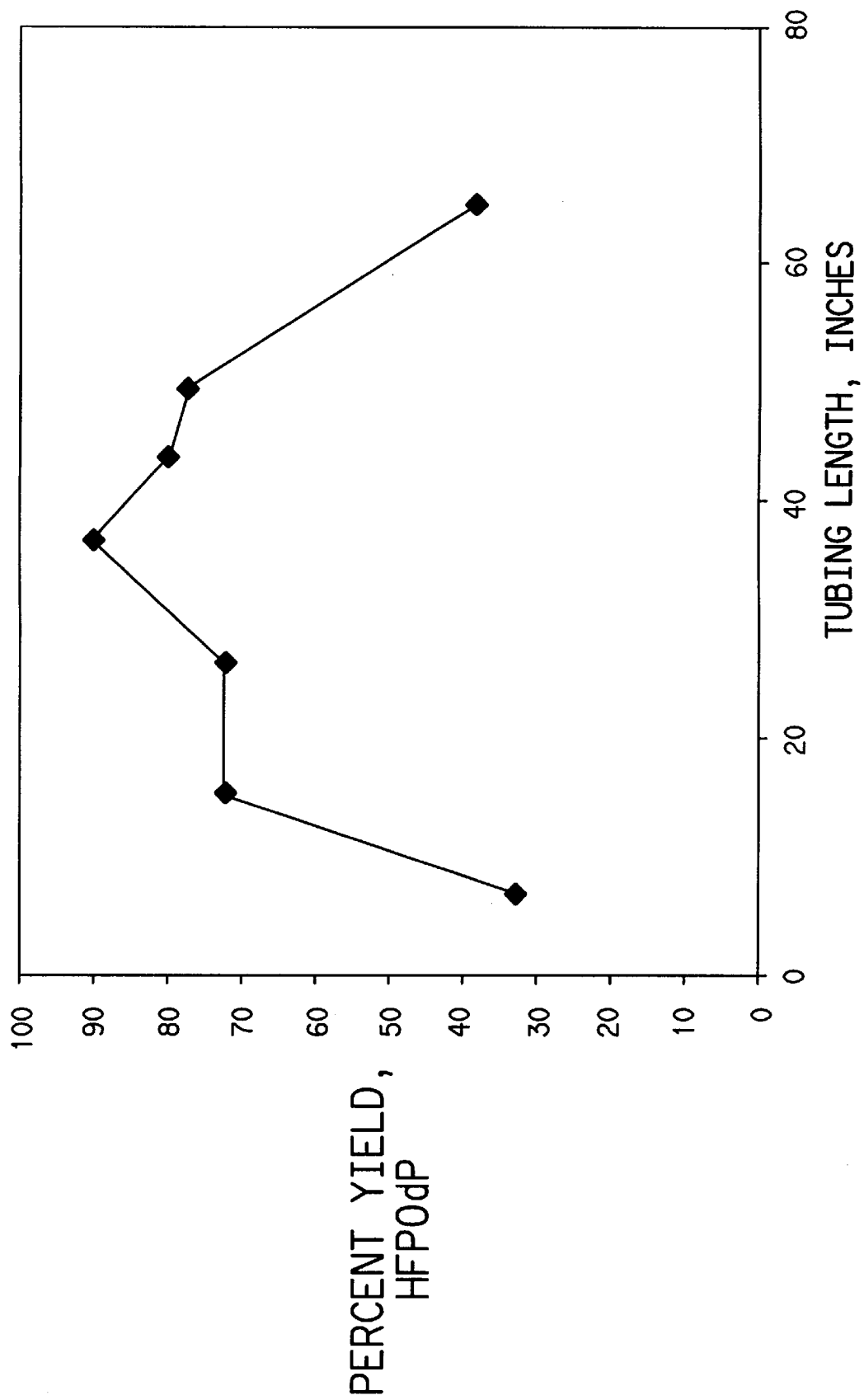
FIG. 2 is a graph of the relationship between percent yield HFPOdP and tubing length, in inches.

As mentioned above, in the continuous process, the reactants are contacted in the reactor but the process may shift a portion of the reaction from the reactor to the transfer lines where the reaction is substantially completed. The dimensions of the transfer lines are critical to promote continuance of the reaction. Reaction in the tranfer lines will continue only so long as the organic and aqueous phases remain intimately mixed. This can only occur where the movement of the fluid through the line allows enough turbulance to counter the natural tendency of the organic and aqueous phases to separate. In Example 11(B) described below, for example, a stream of $KOH/H_2O_2$ is contacted with a stream of HFPO dimer acid fluoride in a Hoke® T fitting that serves as a jet mixer. The reaction is carried from the jet mixer through stainless steel tubing with an internal diameter of about 0.085 inch. Table 1 and FIG. 2 show how the yield of HPFO dimer peroxide varies with the length of the tubing. In this example, 38 inches is the optimum length. The reactants must stay in the line or reaction vessel long enough to approach completion but not so long that the competing processes decrease yield. See, for example, the discussion in U.S. Pat. No. 5,399,643, column 1, lines 25–28, which is incorporated herein by reference.

In an embodiment, such as described by Example 11(B), a few yardsticks can be used to demonstrate the magnitude of the improvement claimed herein. The ⅛" Hoke® fitting is about the size of a man's thumb. The line running from the reactor that receives the reactants and in which the reaction is completed resembles several lengths of spaghetti. Within this very small reaction volume (about 3.4 ml.) enough peroxide is generated to run a commercial scale fluoropolymer plant on a commercial basis. It is clear that if the ⅛" Hoke® fitting could be scaled up to a volume of one gallon, the rate of fluid flow through the reactor would be about 87,000 gallons per hour. When compared to the rates taught in the art, Example 11(B) makes HFPOdP at 57,000 lbs/gal/hr as compared to 36/lbs/gal/hr for U.S. Pat. No. 2,792,423 (making fluorocarbon peroxides) and 1,300,000 gms/gal/hr as compared to 80–120 gms/gal/hr, of active oxygen content, for U.S. Pat. No. 4,075,236 (making hydrocarbon peroxides). Thus, the productivity of the process of Example 11(B) is about 1000 times the productivity of the nearest art.

Optimum flow rate through the lines is a function of a number of chemical and mechanical variables. These variables include the degree of initial turbulence in the fluid that enters the tranfer line (i.e., tube), fluid densities and viscosities, the kinetics of peroxide formation, the kinetics of peroxide degradation, the absence or presence of surface active by-products during hydrolysis, the presence of added surfactants or phase transfer catalysts, reactant concentrations, the identity of the counterions, the identity of the organic phase, the rate of transfer of organic and inorganic species between the aqueous and organic phases and the temperature.

Mixing methods useful in the process are high energy and high shear methods including ultrasonic, jet and static mixing methods (jet and static methods are preferred for continuous processes; ultrasonic methods are preferred for batch processes), and stator/rotors (mechanical mixers). The mixers can be used singly or in series, in batch or continuous processes. Various methods of mixing will work as long as they have enough energy and shear and are conducted rapidly. Ultrasonic mixing methods herein include, but are not limited to, piezoelectric or magnetostrictive transducers coupled to resonant horns and to liquid powered sonic and ultrasonic homogenizers known to those skilled in the art as methods of mixing and homogenizing liquids.

In order for agitation to reduce reaction time to less than one minute, preferably less than thirty seconds in the present process, Reynolds numbers should fall from about 1000 to about 40,000 for the jet mixers and static mixers, and those segments of transfer line within which peroxide formation is completed. Reynolds numbers are dimensionless quantities that characterize fluid flow in pipes or a fluid interacting with other solid bodies, calculated from average fluid velocity, the dimensions of the body or pipe, and the kinetic viscosity of the fluid. For example, in the case of fluid flow through a pipe, the Reynolds number (abbreviated as RN) is calculated from the following formula:

$$RN = \frac{2VR}{N}$$

in which V is the average fluid velocity in the pipe, R is the inside radius of the pipe, and N is the kinetic viscosity.

Reaction temperatures are −10° C. to 40° C. 0° C. to 25° C. are preferred. A desirable feature of the current process is that it runs at substantially ambient temperatures and in some embodiments cooling of the transfer lines can be completely avoided (See Example 11C). The reason the present process can make highly unstable peroxides at ambient temperature where prior art processes can not is the relative speed with which the process makes peroxide and can deliver it for use or storage.

Acyl halides herein are selected from the group consisting of R(C=O)X and RO(C=O)X in which X is —Cl, —F, —Br or —I, preferably —Cl or —F; R is selected from the group consisting of:

(i) $C_nF_xCl_yH_z$, wherein x+y+z=2n+1, n is 1 to 8, linear or branched, carbon bearing —(C=O)X preferably primary;

(ii) G(CF2)$_w$[CF(CF$_3$)CF$_2$]$_x$[OCF(CF$_3$)CF$_2$]$_y$[OCF(CF$_3$)]$_z$— where w is 0 to 8;
x is 0 or 1;
y is 0 to 7;
z is 0 to 1; and
w+x+y+z≧1 and G is a fluorine or a substituted carbon group that is not highly reactive toward water, hydroxide, or hydrogen peroxide and having one or more functional groups such as, but not limited to, —F, —COOCH$_3$, —SO$_2$F, H, —Br, —CFBrCF$_2$Br (x=0), —Cl, —I, —CN, —OC$_6$F$_5$; and (iii) an aromatic, hydro, chloro or perfluoro carbon compound having the same functional groups listed directly above.

Acid halide groups with higher molecular weight alkyl groups are preferred in the process for hydrolytic stability when making aqueous dispersions of fluorocarbon peroxides.

The bases useful herein are strong bases in water. They include metal or tetralkyl ammonium hydroxide or water soluble equivalents. The bases used are preferably >0.1 molar in water. 1 to 5 molar base (for example 15–23 wt % in the case of KOH) is most preferred. For fluorocarbon processes KOH and LiOH are most preferred. NaOH, CsOH and $R'_4N+OH^-$, where $R'$ is $CH_3$ and $C_2H_5$— are acceptable. For hydrocarbons, useful bases are $R'_4N+$, where $R'$ is $CH_3$, $C_2H_5$—, or $CH_3CH_2CH_2CH_2$— and KOH, LiOH, NaOH, and CsOH.

Preferred peroxide reactants are the $H_2O_2$ and t-BuOOH. The peroxides are preferably water soluble.

Solvents useful in the reaction are those that are unreactive with peroxides and that readily solubilize the peroxide. Solvents can be, for example, gases such as hexafluoropropylene if the reaction mixture is held under sufficient pressure to maintain a liquid phase. No organic solvent is needed if the peroxide is stable enough to be handled safely pure (See Examples 53 and 60). Fluorocarbon solvents are, in general, more usefil with fluorinated peroxides and hydrocarbon solvents with hydrocarbon peroxides. In general, solvents are selected from a group of organic fluids characterized by their inertness toward the reactants, their ability to dissolve at least 1% of the peroxide by weight and their acceptability in common end use applications for the peroxides. Suitable solvents are, for example, selected from the group consisting of Freon® E1, Freon® E2, Freon® 113, fluorocarbons, chlorofluorocarbons, hydrofluorocarbons, hydrofluorochlorocarbons, hexane, cyclohexane and mineral spirits.

Surfactants increase yield in some cases. Suitable surfactants include fluorinated surfactants and hydrocarbon surfactants. A preferred group consists of ammonium perfluorooctanoate and sodium dodecyl sulfate.

Ratios of reactants vary based on the structures of the reactants. U.S. Pat. No. 2,792,423, which is incorporated herein by reference, claims a ratio of 1 to 2 equivalents of base to acid halide. With HFPOdP an 8 fold excess of base over acid halide is useful. The optimum equivalents of base to equivalents of acid fluoride for this process falls within a 1:1 to 1:10 ratio. In the case of HFPOdP, peroxide is made in greater than a 50–90% yield using from 1 to 10 equivalents of base per equivalent of acid halide. It is expected that diminishing yields can be made outside these bounds. For the particular equipment and conditions described in Example 11(B) the preferred ratio of base to acid fluoride was about 4 to 9 with the most preferred ratio about 6.5.

Aqueous dispersions of perfluorodiacyl peroxides are among the useful products of the present process. It has been observed that the higher molecular weight peroxide used in a dispersion the longer the peroxide survives before significant hydrolysis results. Thus, for many aqueous applications, it is expected that the higher molecular weight peroxides will be the most useful.

In summary, using selected mixing methods, individually or in series, in batch or continuous processes, a rapid method as been developed that is uniquely suited to production and delivery of highly unstable peroxide structures by providing production and delivery of the peroxide in less than one minute and in many cases less than 30 seconds. This is surprising, particularly in the case of perfluoro acyl peroxides since the high intensity mixing and strongly basic conditions would be expected to exacerbate peroxide loss to hydrolysis. Particular advantages to the continuous process herein are the fact that the process shifts a significant portion of the reaction to the transfer lines. The processes improve the safety of the manufacture of the peroxides by increasing productivity while avoiding large peroxide inventories, and in some cases avoiding the need for refrigeration. The continuous processes described herein [as shown in Example 11(c)] particularly when used in the absence of heating or cooling facilities, can be conveniently used as a portable process.

Some of the novel peroxides produced by the present process are of the following structure:

$$\{G(CF_2)_w[CF(CF_3)CF_2]_x[OCF(CF_3)CF_2]_y[OCF(CF_3)]_z(C=O)O-\}_2$$

w is 0 to 8;
x is 0 or 1;
y is 0 to 7;
z is 0 to 1; and
w+x+y+z>1.

Specific embodiments claimed herein are of the above structure wherein G, w, x, y and z are as indicated below:

$G=CH_3OOC-$
w is 1 to 4
x is 0
y is 0 to 7
z is 1
$G=BrCF_2CFBr-$
w is 0
x is 0
y is 0 to 7
z=1
$G=C_6F_5O-$
w is 0
x is 0
y is 0 to 7
z is 1
G is I—
w is 2 to 8
x is 0
y is 0 to 7
z is 0 or 1 (z is 1 when y>0)

Among the specific novel compounds claimed herein that fall within the above definitions are the following:
$[CH_3O(C=O)CF_2CF_2OCF(CF_3)CF_2OCF(CF_3)(C=O)O]_2$,
$[CH_3O(C=O)CF_2CF_2OCF(CF_3)(C=O)O]_2$, $[ICF_2CF_2(CO)O]_2$
$[C_6F_5OCF(CF_3)CF_2OCF(CF_3)(CO)O]_2$ and
$[BrCF_2CFBrOCF_2CF(CF_3)OCF_2CF_2(CO)O]_2$.

DEFINITIONS

The following acronyms and tradenames are employed in the experimental descriptions.

HFPOCOF, HFPO Dimer Acid Fluoride: $CF_3CF_2CF_2OCF(CF_3)COF$
HFPOdP, HFPO Dimer Peroxide: $[CF_3CF_2CF_2OCF(CF_3)(C=O)O]_2$
Freon® E1: $CF_3CF_2CF_2OCFHCF_3$
Freon® E2: $CF_3CF_2CF_2OCF_2CF(CF_3)OCFHCF_3$
Freon 113: $CFCl_2CF_2Cl$
4P, Perfluorobutyryl Peroxide: $[CF3CF2CF2(C=O)O]_2$
3P, Pefluoropropionyl Peroxide, $[CF_3CF_2(C=O)O]_2$
IBP, Isobutyryl Peroxide, $[(CH_3)_2CH(C=O)O]_2$
EtHDC, bis-(2-Ethylhexyl)peroxydicarbonate
$[CH_3CH_2CH_2CH_2CH(C_2H_5)CH_2O(C=O)O]_2$
FC-143: $C_7F_{15}COONH_4$
DAE, Methyl Perfluoro[8-(fluoroformyl)-5-methyl-4,7-dioxanonanoate],
$CH_3O(C=O)CF_2CF_2OCF(CF_3)CF_2OCF(CF_3)COF$ DAEP, Diacyl peroxide from DAE:
  [CH$_3$O(C=O)CF$_2$CF$_2$OCF(CF$_3$)CF$_2$OCF(CF$_3$)(C=O)O]$_2$
MAE, Methyl perfluoro [5-(fluoroforinyl)-4-oxahexanoate],
  CH$_3$O(C=O)CF$_2$CF$_2$OCF(CF$_3$)COF
MAEP, Diacylperoxide from MAE,
  [CH$_3$O(C=O)CF$_2$CF$_2$OCF(CF$_3$)(C=O)O]$_2$
SF, FSO$_2$CF$_2$CF$_2$OCF(CF$_3$)CF$_2$OCF(CF$_3$)COF
SFP, Diacylperoxide from SF
  [FSO$_2$CF$_2$CF$_2$OCF(CF$_3$)CF$_2$OCF(CF$_3$)(CO)O]$_2$
7HCl, 7-H-Perfluoroheptanoyl Chloride, H(CF$_2$)$_6$COCl
7HP, Diacylperoxide from 7HCl, H(CF$_2$)$_6$(CO)OO(CO)(CF$_2$)$_6$COCl
BrCl, BrCF$_2$CFBrOCF$_2$CF(CF$_3$)OCF$_2$CF$_2$COCl
BrP, Diacylperoxide from BrCl, [BrCF$_2$CFBrOCF$_2$CF(CF$_3$)OCF$_2$CF$_2$(CO)O]$_2$
IF, 3-Iodoperfluoropropionylfluoride, ICF$_2$CF$_2$COF
IP, [ICF$_2$CF$_2$(CO)O]$_2$
PhenoxyCOF, C$_6$F$_5$OCF(CF$_3$)CF$_2$OCF(CF$_3$)COF
PhenoxyP, [C$_6$F$_5$OCF(CF$_3$)CF$_2$OCF(CF$_3$)(CO)O]$_2$
t-Butylperacetate, CH$_3$(C=O)OOC(CH$_3$)$_3$
5Cl, H(CF2)$_4$CH$_2$O(C=O)Cl
5PDC, Peroxydicarbonate from 5Cl: H(CF2)$_4$CH$_2$O(C=O)OO(C=O)CH$_2$(CF$_2$)$_4$H
5COF, a mixture of CF$_3$CF(COF)CF$_2$CF$_2$CF$_3$ and CF$_3$CF$_2$CF(COF)CF$_2$CF$_3$
5P, the peroxide mixture from 5COF, [CF$_3$CF$_2$(CF$_3$CF$_2$CF$_2$)CF(CO)O-]$_2$ and
  [(CF$_3$CF$_2$)$_2$CF(CO)O-]$_2$

EXAMPLES

The following Examples were conducted in the apparatus described by FIG. 1, where numbered structures are as indicated above.

Example 1
Continuous Reactor Preparation of HFPO Dimer Peroxide in Freone® E2
Mixing T Followed by Ultrasonic Mixer The three reactants, aqueous H$_2$O$_2$, aqueous KOH, and HPFOCOF were simultaneously pumped though a mixing T to an ultrasonic cell and then to a product collector, all in about 1 to 30 seconds. A detailed description of the process is given below with reference to the numbered parts in the attached reactor schematic (FIG. 1). It should be flrher noted that the schematic is not meant to be limiting. For example, gear pumps could be used in the place of syringe pumps or the ultrasonic reaction cavity pictured as the reactor could just as well be a jet mixer, a static mixer, an ultrasonic whistle (homogenizer), a mechanical mixer (stator/rotor), or absent altogether (see Example 9 below). The essence of our continuous process is the rapid transit of precisely metered flows of reactants through one or more zones of intense mixing.

Syringe pump (3), loaded with 15% by weight aqueous H$_2$O$_2$, was started up at 0.55 ml/min. Syringe pump (2), loaded with 24% by weight aqueous KOH, was started up at 1.00 ml/min. Syringe pump (1), loaded with 4% by weight HFPO dimer acid fluoride in Freon® E2, was started up at 3.30 ml/min. The streams from the three pumps, chilled with wet ice, were joined into a single stream at a ⅛th" union cross Hoke® fitting (4), a design feature possibly having an unintended effect on yield as can be seen from Example 9 below. The ratio of reactants at this point was 4 moles of H$_2$O$_2$: 8 moles of KOH: 1 mole of HFPOCOF, making for an 8 fold excess of both H$_2$O$_2$ and KOH over HFPOCOF in terms of reaction stoichiometry. Immediately after exiting union cross (4) at 0° C., the liquid stream was run via an 0.035" I.D. line of ~0.1 ml volume into the bottom cup of the 1.6 ml ultrasonic reactor cavity (5) also chilled with wet ice. The power source to the ⅜" diameter ultrasonic horn (6) was turned on providing 18 to 20 watts of power to the ultrasonic cavity. Product exited as a stream at the top of the ultrasonic cavity at 2° C. with an average residence time in the cavity of 20 seconds. The reactor was run for several minutes to flush out the lines and achieve steady operating conditions, this foreshot being run into waste poly container (7). The reactant stream was then diverted to sampling container (8) where 97 ml of effluent were collected for product analysis. The organic layer was separated and washed twice with 75 ml of 5% aqueous sodium bicarbonate. This gave 63 ml of 0.093 M HFPOdP in Freon® E2 for a 93% yield based on starting HFPOCOF.

Using the equipment described in Example 1 above, >70% yields of HFPOdP were obtained using a variety of residence times, stoichiometric ratios, concentrations, solvents, and methods of mixing, typical results being gathered in Table 1 below. In several of these runs the ultrasonic cavity (5) and ultrasonic horn (6) pictured in the reactor schematic were replaced by a 27 element Kenics static mixer having an internal volume of 1.4 ml. Other static mixer designs should function equally well.

TABLE 1

Continuous Reactor Preparation of HFPOdP in Freon ® E1 and Freon ® E2

| Ex | WT % CONCENTRATIONS | | | MOLAR RATIOS[1] | FREON ® | RESIDENCE TIME[5] | MIXER | YIELD HFPOdP[2] |
| --- | --- | --- | --- | --- | --- | --- | --- | --- |
| | H2O2 | KOH | HFPOCOF | | | | | |
| 1 | 15% | 24% | 4% | 4/8/1 | E2 | 20 sec | Ultrasonic | 93.3% |
| 2 | 10% | 18% | 6% | 2.5/5/1 | E2 | 11.5 sec | Ultrasonic | 91.5%[3] |
| 3 | 5% | 12% | 8% | 1/2/1 | E2 | 20 sec | Ultrasonic | 89.1%[4] |
| 4 | 5% | 24% | 4% | 1/2/1 | E2 | 3 sec | Ultrasonic | 87.8% |
| 5 | 30% | 30% | 8.1% | 1.2/2.1/1 | E1 | 16.2 sec | Ultrasonic | 82.9% |
| 6 | 30% | 30% | 16.3% | 1.2/2.1/1 | E1 | 28.2 sec | Ultrasonic | 82.3% |
| 7 | 15% | 24% | 4% | 1/2/1 | E2 | 2.6 sec | Static | 73.3% |
| 8 | 15% | 24% | 4% | 1/2/1 | E2 | 1.3 sec | Static | 74.6% |

[1]Relative molar ratios of H2O2/KOH/HFPOCOF in starting reactant mix
[2]Yield of HFPOdP based on starting quantity of HFPOCOF
[3]Yield = 91.5 ± 7.5%, average of 5 runs (85.1, 87.6, 88.0, 103.9, 92.8)

TABLE 1-continued

Continuous Reactor Preparation of HFPOdP
in Freon ® E1 and Freon ® E2

| Ex | WT % CONCENTRATIONS | | | MOLAR RATIOS[1] | FREON ® | RESIDENCE TIME[5] | MIXER | YIELD HFPOdP[2] |
|---|---|---|---|---|---|---|---|---|
|  | H2O2 | KOH | HFPOCOF | | | | | |

[4]Yield = 89.1 + 2.1%, average of 3 runs (89.5, 91.7, 86.21)
[5]Based on the 1.6 ml volume of ultrasonic cavity, ignoring the volume of the mixing T (~0.2 ml and the volume of the line to the cavity

Example 9
Continuous Reactor Preparation of HFPO Dimer Peroxide in Freon® E2

Turbulent Mixing in Mixing T Alone

The same equipment as in Example 1 was used except that no power was supplied to the ultrasonic horn. The ultrasonic cavity thus became a dead volume providing residence time for further reaction after reactants exited the union cross fitting serving as a mixing T.

Syringe pump (3), loaded with 5% by weight aqueous $H_2O_2$, was started up at 6.07 ml/min. Syringe pump (2), loaded with 24% by weight aqueous KOH, was started up at 3.47 ml/min. Syringe pump (1), loaded with 8% by weight HFPO dimer acid fluoride in Freon® E2, was started up at 22.87 ml/min. The streams from the three pumps, chilled with wet ice, were joined into a single stream at a 1/8th" union cross Hoke® fitting (4) just after having passed though a minimum constriction of 0.09" inch. The ratio of reactants at this point was 4 moles of $H_2O_2$: 8 moles of KOH: 1 mole of HFPOCOF, making for an 8 fold excess of both $H_2O_2$ and KOH over HFPOCOF in terms of reaction stoichiometry. Immediately after exiting union cross (4) at 0° C., the liquid stream was run via an 0.035" I.D. line of ~0.1 ml volume directly into the bottom of a 1.6 ml vessel (the ultrasonic reactor cavity with no power to the horn) chilled in wet ice. Product exited at the top of the cavity at 2° C. with an average residence time in the reactor cavity of 3 seconds. The continuous reactor was run for several minutes to flush out the lines and achieve steady operating conditions, this foreshot being run into waste poly container (7). The reactant stream was then diverted to sampling container (8) where 97 ml of effluent were collected for product analysis. The organic layer was separated and washed twice with 75 ml of 5% aqueous sodium bicarbonate. This gave 65 ml of 0.118 M HFPOdP in Freon® E2 for a 58.5% yield based on starting HFPOCOF.

Example 10
Continuous Reactor Preparation of HFPO Dimer Peroxide in Freon® E2

Mixing T Followed by Static Mixing

The same equipment as in Example 1 was used except that two 27-element Kenics mixers, each with an internal volume of 1.4 ml, were substituted for the ultrasonic reactor.

Syringe pump (3), loaded with 5% by weight aqueous $H_2O_2$, was started up at 37.5 ml/min. Syringe pump (2), loaded with 24% by weight aqueous KOH, was started up at 21.4 ml/min. Syringe pump (1), loaded with 4% by weight HFPO dimer acid fluoride in Freon® E2, was started up at 70.7 ml/min. The streams from the three pumps, chilled with wet ice, were joined into a single stream at a 1/8th" union cross Hoke® fitting (4). Turbulent mixing in the Hoke® fitting alone may initiate some reaction as can be seen from Example 9 above. The ratio of reactants at this point was 4 moles of $H_2O_2$: 8 moles of KOH: 1 mole of HFPOCOF, making for an 8 fold excess of both $H_2O_2$ and KOH over HFPOCOF in terms of reaction stoichiometry. Immediately after exiting union cross (4) at 0° C., the liquid stream was run via an 0.035" I.D. line of ~0.1 ml volume to two Kenics mixers in series, each having an internal volume of 1.4 ml and containing 27 mixing elements in a 3/16" O. D.×7.5" long stainless steel tube. Product exited the two static mixers at 6° C. with an average residence time in the two static mixers of 1.3 seconds. The reactor was run for several minutes to flush out the lines and achieve steady operating conditions, this foreshot being run into waste poly container (7). The reactant stream was then diverted to sampling container (8) where 130 ml of effluent were collected for product analysis. The organic layer was separated and washed twice with 75 ml of 5% aqueous sodium bicarbonate. This gave 70 ml of 0.087 M HFPOdP in Freon® E2 for a 90.5% yield based on starting HFPOCOF.

When flow rates of all the reagent streams were decreased 2× increasing residence time in the static mixers to 2.6 seconds, the yield of peroxide decreased to 86.9%.

Example 11
Continuous Reactor Preparation of HFPO Dimer Peroxide in Freon® E2

A. Jet Mixer Alone, 0° C.: The same equipment was used as in Example 1 except that the $H_2O_2$ and KOH streams were combined prior to mixing with the organic stream and union cross (4) and ultrasonic reactor (5) have been replaced by ajet mixer. The jet mixer was a 1/8" Hoke® T with an internal diameter of 0.094" and an internal length of 0.76", making for an internal volume of 0.086 ml. In these runs the organic phase was pumped straight through the 1/8" Hoke® T at 66.5 ml/minute. The combined aqueous KOH/$H_2O_2$ phase was pumped into the 1/8" Hoke® T at 63.1 ml/min via an 0.044" I.D. tube set 90° to the organic flow. Reducing the diameter of the tubing entering the side inlet of the T to 0.044" provides the orifice dimensions required for jet mixing at the flow rates given above and for the viscosities/densities of the fluids.

Syringe pump (3), loaded with 15% by weight aqueous $H_2O_2$, was started up at 22.8 ml/min. Syringe pump (2), loaded with 24% by weight aqueous KOH, was started up at 40.3 ml/min. Using a 27 element Kenics static mixer, the KOH and $H_2O_2$ streams were combined to a single aqueous stream flowing at 63.1 ml/min. Syringe pump (1), loaded with 8% by weight HFPO dimer acid fluoride in Freon® E2, was started up at 66.5 ml/min. Using 0.044" I.D. tubing, the combined aqueous stream was passed into the side arm of the Hoke® T at 63.1 ml/min impinging into the organic stream moving straight through the Hoke® T at 66.5 ml/min. The ratio of reactants at this point was 4 moles of $H_2O_2$: 8 moles of KOH: 1 mole of HFPOCOF, making for an 8 fold excess of both $H_2O_2$ and KOH over HFPOCOF in terms of reaction stoichiometry. The liquid stream exiting the Hoke® T at ~7° C. was run via an 0.085" I.D. line of ~3.3 ml volume to the collection bottle. The 0.085" diameter of the exit line is such that the turbulent flow may persist after the jet mixer, although this was not confirmed by experiment. Average residence time in the reactor was 0.04 seconds considering just the volume of the Hoke® T serving as the jet mixer or 1.6 seconds considering the volume of the jet mixer and the exit lines together. The continuous reactor was run for 1.5 minutes to flush out the lines and achieve steady operating conditions, this foreshot being run into waste poly container (7). The reactant stream was then diverted to sampling container (8) where 65 to 64 ml of organic phase were collected over the next minute for purposes of product analysis. The organic layer was separated and washed twice with 75 ml of 5% aqueous sodium bicarbonate. Over the course of two separate runs this gave solutions 0.173 M and 0.167 M in HFPOdP in Freon® E2 for yields of 89 and 84% respectively based on starting HFPOCOF.

Making ~65 ml of 0.167 M HFPOdP in a volume of 0.086 ml in a minute corresponds to a productivity of 43,000 lbs of HFPOdP/gallon/hr. The fastest comparable prior art we are aware of, U.S. Pat. No. 2,792,423, reports making 7.2 g of 4 P/100 ml/min for a productivity of 36 lbs of 4 P/gallon/hr. Putting this in the language of U.S. Pat. No. 4,075,236, a productivity of 36 lbs of 4P/gal/hr is equal to ~1200 g of active oxygen content/gal/hr and a productivity of 43,000 lbs of EFPOdP/gal/hr is equal to 950,000 g of active oxygen content/gal/hr.

B. Jet Mixer Alone, 26° C.: The same equipment was used as in Example 1 except that the $H_2O_2$ and KOH streams were combined prior to mixing with the organic stream, union cross (4) and ultrasonic reactor (5) have been replaced by a jet mixer, and the 0° C. ice bath has been replaced by a 26° C. water bath. The jet mixer was a ⅛" Hoke® T with an internal diameter of 0.094" and an internal length of 0.76", making for an internal volume of 0.086 ml. In these runs the organic phase was pumped straight through the ⅛" Hoke® T at 125 ml/minute. The combined aqueous KOH/$H_2O_2$ phase was pumped into the ⅛" Hoke® T at 85.0 ml/min via an 0.038" I.D. tube set 90° to the organic flow. Reducing the diameter of the tubing entering the side inlet of the T to 0.038" provides the orifice dimensions required for jet mixing at the flow rates given above and for the viscosities/densities of the fluids.

Syringe pump (3), loaded with 12.9% by weight aqueous $H_2O_2$, was started up at 31.2 ml/min. Syringe pump (2), loaded with 18.3% by weight aqueous KOH, was started up at 53.8 ml/min. Using a 27 element Kenics static mixer, the KOH and $H_2O_2$ streams were combined to a single aqueous stream flowing at 85.0 ml/min. Syringe pump (1), loaded with 5% by weight HFPO dimer acid fluoride in Freon® E2, was started up at 125.0 ml/min. Using 0.038" I.D. tubing, the combined aqueous stream was passed into the side arm of the Hoke® T at 85.0 ml/min impinging into the organic stream moving straight through the Hoke® T at 125.0 ml/min. The ratio of reactants at this point was 4 moles of $H_2O_2$: 6.5 moles of KOH: 1 mole of HFPOCOF, making for a large excess of both $H_2O_2$ and KOH over HFPOCOF in terms of reaction stoichiometry. The liquid stream exiting the Hoke® T at 31° C. was run via an 0.085" I.D. line of ~3.3 ml volume to the collection bottle. The 0.085" diameter of the exit line is such that the turbulent flow may persist after the jet mixer, although this was not confirmed by experiment. Average residence time in the reactor was 0.025 seconds considering just the volume of the Hoke® T serving as the jet mixer or 0.97 seconds considering the volume of the jet mixer and the exit lines together. The continuous reactor was run for 1.5 minutes to flush out the lines and achieve steady operating conditions, this foreshot being run into waste poly container (7). The reactant stream was then diverted to sampling container (8) where 121 ml of organic phase were collected over the next minute for purposes of product analysis. The organic layer was separated and washed twice with 75 ml of 5% aqueous sodium bicarbonate. Iodometric titration found 0.118M HFPOdP in Freon® E2 for a yield of 95.5% based on starting HFPOCOF.

Making 121 ml of 0.118 M HFPODP in a volume of 0.086 ml in a minute corresponds to a productivity of 57,000 lbs of HFPOdP/gallon/hr. The fastest comparable prior art we are aware of, U.S. Pat. No. 2,792,423, reports making 7.2 g of 4 P/100 ml/min for a productivity of 36 lbs/gallon/hr. Putting this in the language of U.S. Pat. No. 4,075,236, a productivity of 36 lbs of 4 P/gal/hr is equal to ~1200 g of active oxygen content/gal/hr and a productivity of 57,000 lbs of HFPOdP/gal/hr is equal to 1,300,000 g of active oxygen content/gal/hr.

In Example 11B, the reaction mixture is carried from the jet mixer to the product collection vessel via a 38" length of stainless steel tubing with an internal diameter of 0.085 inch. The table below shows how the yield of HPFO dimer peroxide varies with the length of tubing. The same data is graphed in FIG. 2 wherein tubing length is related to yield of HFPOdP.

Optimum transferline length for this particular reactor configuration and transferline diameter is about 38 inches. With shorter transferlines, the reaction does not have time to go to completion and yields can be significantly lower. Clearly, much of the HFPO dimer peroxide is being formed in the transferline following the jet mixer. For purposes of productivity calculations it is, perhaps, more accurate then to consider the true reactor volume to be the combined volume of the jet mixer and its following transferline, about 3.3 ml in this instance. Using 3.3 ml as the reactor volume in this example makes our productivity about 1400 lbs of HFPOdP/gal/hour or 31,000 g of active oxygen content/gallon/hr, still large increases over prior art.

Effect of Transfer Line Length on HFPOdP Yield

| Tubing Length | Yield of HFPOdP |
| --- | --- |
| 6" | 33.3% |
| 16" | 72.2% |
| 27" | 72.1% |
| 38" | 90.3% ± 4.6% |
| 45" | 80.4% |
| 51" | 77.8% |
| 64" | 39.1% |

C. Jet Mixer Alone, ambient temperature: Part B immediately above was repeated with no temperature control on the monomer feeds, the jet mixer, or transfer line to the collection vessel. Ambient temperature the day of the run was 24° C. and product exiting the reactor had a temperature of 30° C., 121 ml of organic phase being collected. The organic layer was separated and washed twice with 75 ml of 5% aqueous sodium bicarbonate. Iodometric titration found 0.103 M HFPOdP in Freon® E2 for a yield of 83.8% based on starting HFPOCOF.

Making 121 ml of 0.103 M HFPOdP in a volume of 0.086 ml in a minute corresponds to a productivity of 48,000 lbs of HFPOdP/gallon/hr. The fastest comparable prior art we are aware of, U.S. Pat. No. 2,792,423, reports making 7.2 g of 4 P/100 ml/min for a productivity of 36 lbs/gallon/hr. Putting this in the language of U.S. Pat. No. 4,075,236, a productivity of 36 lbs of 4 P/gal/hr is equal to ~1200 g of active oxygen content/gal/hr and a productivity of 48,000 lbs of HFPOdP/gal/hr is equal to 1,100,000 g of active oxygen content/gal/hr.

Example 12
Continuous Reactor Preparation of HFPO Dimer Peroxide in Freon® E2
    Jet Mixer in Series with Static Mixer
    HFPOdP was prepared in exactly the same apparatus under the same conditions as in Example 11A except that the line leaving the jet mixer was replaced by two Kenics static mixers in series, each having an internal volume of 1.4 ml and containing 27 mixing elements in a 3/16" O.D.×7.5" long stainless steel tube. Yields over the course of two runs, 86.5 and 86.8%, were essentially the same within experimental error as those obtained with the jet mixer alone in Example 11A above.

Example 13
Continuous Reactor Preparation of 3P in Freon® E1
    Mixing T Followed by Ultrasonic Mixer or Static Mixer
    A solution containing ~8 wt % perfluoropropionyl chloride dissolved in Freon® E1 was first prepared. A 1 liter stainless steel cylinder containing 747 ml (1142 g) of Freon® E1 was chilled on dry ice, evacuated, and 98.1 g of perfluoropropionyl chloride distilled in. Assuming all the perfluoropropionyl chloride to have dissolved in the Freon® E1 with a density on its part of 1.3 g/ml at room temperature, the final solution should then have a net volume of 747 ml of E1+75.5 ml $C_2F_5COCl$=~822 ml and a net weight of 1142 g E1+98.1 g $C_2F_5COCl$=1240 g, giving ~0.67 M $C_2F_5COCl$ in Freon® E1. At the room temperature the pressure in such cylinders has been found to be about 5 psig. Using PV=nRT this implies that each 100 ml of vapor space in the cylinder will contain at most 1 g of $C_2F_5COCl$ lost from the Freon® E1 phase. For purposes of yield calculations this loss of $C_2F_5COCl$ to the vapor phase was ignored, although it should be kept in mind that this loss of $C_2F_5COCl$ to the vapor phase will make yields appear a bit lower than they actually are.
    Syringe pump (3), loaded with 5% by weight aqueous $H_2O_2$, was started up at 16.64 ml/min. Syringe pump (2), loaded with 24% by weight aqueous KOH containing 0.6 g of FC-143 surfactant (perfluorooctanoic acid ammonium salt)/100 ml, was started up at 9.46 ml/min. Syringe pump (1), loaded with ~8% by weight $C_2F_5COCl$ in Freon® E1, was started up at 37.8 ml/min. The streams from the three pumps, chilled with wet ice, were joined into a single stream at a ⅛th" union cross Hoke® fitting (4). The ratio of reactants at this point was 1 mole of $H_2O_2$: 2 moles of KOH: 1 mole of HFPOCOF, making for a 2 fold excess of both $H_2O_2$ and KOH over HFPOCOF in terms of reaction stoichiometry. Immediately after exiting union cross (4), the liquid stream was run via an 0.035" I.D. line of ~0.1 ml volume into the bottom cup of the 1.6 ml ultrasonic reactor cavity (5) also chilled with wet ice. The power source to the ⅜" diameter ultrasonic horn (6) was turned on, providing 18 to 20 watts of power to the ultrasonic cavity. Product exited as a stream at the top of the ultrasonic cavity at 18–19° C. (having entered at 8° C.) with an average residence time in the cavity of 1.5 seconds. The reactor was run for several minutes to flush out the lines and achieve steady operating conditions, this foreshot being run into waste poly container (7). The reactant stream was then diverted to sampling container (8) where 69 ml of effluent were collected for product analysis. The organic layer was separated and washed twice with 5% aqueous sodium bicarbonate, and iodometrically titrated as 0.164 M 3P in Freon® E1 for a 43% yield based on an assumed starting $C_2F_5COCl$ concentration of 0.67M.
    A similar run in the absence of FC-143 surfactant gave a 23% yield of 3P. A third run using no surfactant and instead of an ultrasonic mixer a 1.3 sec residence time through two 1.4 ml, 27 element Kenics mixers gave a 18% yield of 3P.

Example 14
Ultrasonic Batch Preparation HFPO dimer Peroxide in Freon® E1
    An ice-chilled, 150 ml beaker (barely large enough) was loaded with 3.01 g of KOH pellets (0.0458 mole) dissolved in 10 ml of water, 78 ml of Freon® E1, and 4.70 ml of 30% aqueous hydrogen peroxide (0.0458 mole). A titanium horn attached to a 150 watt Branson ultrasonic power source was immersed roughly halfway down into the 2" deep pool of reactants. A solution of 7.4 ml of HFPO dimer acid fluoride (0.0352 mole) in 13 ml of Freon® E1 was added. The ultrasonic source was turned on for 30 seconds, drawing roughly 38 watts of power. The layers were then separated and washed twice with 50 ml of ~5% aqueous sodium bicarbonate, layer separations taking 20, 20, and 10 seconds respectively. This gave 68 ml of 0.228 M HFPO dimer peroxide (82% yield based on starting HFPOCOF). Table 1 below summarizes results for Example 14 here and similar runs, Examples 15 to 19, in Freon® E1 and E2 solvents.

TABLE 1

Ultrasonic Batch Preparation HFPOdP in Freon ®E1 and E2 KOH and $H_2O_2$ in Excess

| EX. | MOLAR RATIOS | | | TOTAL | | RXN TIME | YIELD HFPOdP |
|---|---|---|---|---|---|---|---|
| | HFPOCOF | KOH | $H_2O_2$ | FREON ® | $H_2O$ | | |
| 14 | 1 | 1.3 | 1.3 | 91 ml E1 | 10 ml | 30 sec | 82% |
| 15 | 1 | 1.7 | 1.7 | 91 ml E1 | 28 ml | 10 sec | 65% |
| 16 | 1 | 1.7 | 1.7 | 91 ml E | 28 ml | 30 sec | 68% |
| 17 | 1 | 5.1 | 5.1 | 91 ml E1 | 75 ml | 10 sec | 60% |
| 18 | 1 | 17 | 17 | 182 ml E2 | 170 ml | 10 sec | 74% |
| 19 | 1 | 17 | 17 | 182 ml E2 | 170 ml | 30 sec | 78% |

Example 20
Ultrasonic Batch Preparation HFPO dimer Peroxide in Freon® E1
    HFPOCOF in Excess
    An ice chilled beaker was loaded with 1.64 g of KOH pellets (0.024 mole) dissolved in 10 ml of water, 50 ml of Freon® E1, 1.22 ml of 30% aqueous hydrogen peroxide (0.012 mole), and 5.5 ml of HFPOCOF (0.026 mole). A titanium horn attached to a 40 Khz, 150 watt Dukane ultrasonic power source was immersed roughly halfway down into the pool of reactants. The ultrasonic source was turned on for 30 seconds at full power. The layers were then separated and washed twice with 50 ml of ~5% aqueous sodium bicarbonate. This gave 50 ml of 0.156 M HFPO dimer peroxide in Freon® E1 (60% yield based on starting HFPOCOF, 65% yield based on starting $H_2O_2$). When using 5.0 ml of HFPOCOF (0.024 mole) instead of the 5.5 ml reported above, the yield of HFPOdP was 58% based on both the HFPOCOF and the $H_2O_2$.

Example 21
Ultrasonic Batch Preparation 4P in Freon® E1

A. Lithium Hydroxide as Base: A 250 ml beaker was loaded with 2.5 g of lithium hydroxide monohydrate (60 mmoles), 28 ml of water, 0.1 g of ammonium perfluorooctanoate, and 90 ml of Freon® E1 with ice bath cooling. Once solution was complete, 6.13 ml of 30% hydrogen peroxide (60 mmoles) were added with stirring. The solution was chilled again to ~0° C. and then 5.2 ml of perfluorobutyryl chloride (35 mmoles) were added. An ultrasonic horn connected to a 40 Khz, 150 watt Dukane power source was started up at ~50% of maximum power and lowered into the reaction mixture. After 5 seconds, ultrasonication was stopped, the organic layer was separated and washed twice with 50 ml of 5% aqueous $NaHCO_3$. The organic layer had a total volume of 90 ml and was found to be 0.156 M in 4P for an overall yield of 80% based on starting perfluorobutyryl chloride. Producing 90 ml of 0.156 M 4P solution in 5 seconds corresponds to a productivity of 400 lbs of 4P/gal/hr. The best prior art applicants are aware of for 4P, or for that matter any other process for any acyl peroxide, is 36 lb/gal/hr (U.S. Pat. No. 2,792,423).

B. Potassium Hydroxide as Base: A 250 ml beaker was loaded with 3.96 g of 85% KOH pellets (60 mmoles), 28 ml of water, and 90 ml of Freon® E1 with ice bath cooling. Once solution was complete, 6.13 ml of 30% hydrogen peroxide (60 mmoles) were added with stirring. The solution was chilled again to ~0° C. and then 5.2 ml of perfluorobutyryl chloride (35 mmoles) were added. An ultrasonic horn connected to a 40 Khz, 150 watt Dukane power source was started up at ~75% of maximum power and lowered into the reaction mixture. After 15 seconds, ultrasonication was stopped, the organic layer was separated and washed twice with 50 ml of 5% aqueous $NaHCO_3$. The organic layer had a total volume of 88 ml and was found to be 0.150 M in 4P for an overall yield of 76% based on starting perfluorobutyryl chloride.

C. Tetraethylammonium Hydroxide as Base: A beaker was loaded with 15.5 ml of 20% aqueous tetraethylammonium hydroxide (22 mmoles) and 78 ml of Freon® E1 with ice bath cooling. Once solution was complete, 2.35 ml of 30% hydrogen peroxide (23 mmoles) were added with stirring. The solution was chilled again to ~0° C. and then 2.8 ml of perfluorobutyryl chloride (19 mmoles) were added. An ultrasonic horn connected to a 40 Khz, 150 watt Dukane power source was started up at ~100% of maximum power and lowered into the reaction mixture. After 15 seconds, ultrasonication was stopped, the organic layer was separated and washed twice with 50 ml of 5% aqueous $NaHCO_3$. The organic layer had a total volume of 70 ml and was found to be 0.088 M in 4P for an overall yield of 65% based on starting perfluorobutyryl chloride.

D. Tetramethylammonium Hydroxide as Base: A beaker was loaded with 7.9 ml of 25% aqueous tetramethylammonium hydroxide (22 mmoles) and 78 ml of Freon® E1 with ice bath cooling. Once solution was complete, 2.35 ml of 30% hydrogen peroxide (23 mmoles) were added with stirring. The solution was chilled again to ~0° C. and then 2.8 ml of perfluorobutyryl chloride (19 mmoles) were added. An ultrasonic horn connected to a 40 Khz, 150 watt Dukane power source was started up at ~100% of maximum power and lowered into the reaction mixture. After 15 seconds, ultrasonication was stopped, the organic layer was separated and washed twice with 50 ml of 5% aqueous $NaHCO_3$. The organic layer had a total volume of 75 ml and was found to be 0.075 M in 4P for an overall yield of 59% based on starting perfluorobutyryl chloride.

E. Cesium Hydroxide as Base: A 250 ml beaker was loaded with 10.4 ml of 50% aqueous cesium hydroxide (60 mmoles), 20 ml of water, and 90 ml of Freon® E1 with ice bath cooling. Once solution was complete, 6.13 ml of 30% hydrogen peroxide (60 mmoles) were added with stirring. The solution was chilled again to ~0° C. and then 5.2 ml of perfluorobutyryl chloride (35 mmoles) were added. An ultrasonic horn connected to a 40 Khz, 150 watt Dukane power source was started up at ~75% of maximum power and lowered into the reaction mixture. After 15 seconds, ultrasonication was stopped, the organic layer was separated and washed twice with 50 ml of 5% aqueous $NaHCO_3$. The organic layer had a total volume of 88 ml and was found to be 0.112 M in 4P for an overall yield of 56% based on starting perfluorobutyryl chloride.

F. Sodium Hydroxide as Base: A 250 ml beaker was loaded with 2.4 g of NaOH pellets (60 mmoles), 28 ml of water, and 90 ml of Freon® E1 with ice bath cooling. Once solution was complete, 6.13 ml of 30% hydrogen peroxide (60 mmoles) were added with stirring. The solution was chilled again to ~0° C. and then 5.2 ml of perfluorobutyryl chloride (35 mmoles) were added. An ultrasonic horn connected to a 40 Khz, 150 watt Dukane power source was started up at ~75% of maximum power and lowered into the reaction mixture. After 15 seconds, ultrasonication was stopped, the organic layer was separated and washed twice with 50 ml of 5% aqueous $NaHCO_3$. The organic layer had a total volume of 88 ml and was found to be 0.075 M in 4P for an overall yield of 37% based on starting perfluorobutyryl chloride.

Example 22
Ultrasonic Batch Preparation 3P in Freon® E1

A beaker was loaded with 3.96 g of 85% KOH pellets (60 mmoles), 0.1 g of ammonium perfluorooctanoate, 28 ml of water, and 40 ml of Freon® E1 with ice bath cooling. Once solution was complete, 6.13 ml of 30% hydrogen peroxide (60 mmoles) were added with stirring. The solution was chilled again to ~0° C. and then 87.5 g of a Freon® E1 solution containing 6.88 g of perfluoropropionyl chloride (38 mmoles) were added. An ultrasonic horn connected to a 40 Khz, 150 watt Dukane power source was started up at ~75% of maximum power and lowered into the reaction mixture. After 30 seconds, ultrasonication was stopped. The organic layer separated immediately and was washed twice with 50 ml of 5% aqueous $NaHCO_3$. The organic layer had a total volume of 85 ml and was found to be 0.136 M in 3P by iodometric titration for an overall yield of 61% based on starting perfluoropropionyl chloride.

Example 23
Ultrasonic Batch Preparation of HFPOdP as Aqueous Dispersion

A beaker was loaded with 1.78 g of 85% KOH pellets (27 mmoles), 0.1 g of ammonium perfluorooctanoate, and 60 ml of water. Once solution was complete the mixture was chilled on ice and 1.4 ml of 30% hydrogen peroxide added (14 mmoles) and then 5.0 ml of HFPO dimer acid fluoride (23.8 mmoles). An ultrasonic horn connected to a 40 Khz, 150 watt Dukane power source was started up at ~100% of maximum power and lowered into the reaction mixture. After 30 seconds the power was turned off to the ultrasonic horn and the white dispersion stirred gently while cooling on ice for a 1 minute ripening period. Fifty ml of Freon® 113 were added to the reaction mixture.* The reaction mixture was then transferred to a separatory funnel and shaken vigorously completing transfer of HFPOdP to the Freon® 113 layer. After washing twice with 50 ml of 5% aqueous $NaHCO_3$, the organic layer had a total volume of 50 ml and was found to be 0.150 M in HFPOdP by iodometric titration, giving a 63% yield of HFPOdP based on starting HFPOCOF and accounting for 53% of the starting $H_2O_2$. Returning to the original water layer, its volume was found to be 60 ml and iodometric titration found it to be 0.110 M in peroxide, accounting for the remaining 47% of the starting $H_2O_2$. The peroxide in the aqueous phase is likely either unreacted hydrogen peroxide, the peroxy acid sodium salt $CF_3CF_2CF_2OCF(CF_3)(C=O)OO^-Na^+$, or a mixture of the two. Indeed in a similar run, acidification of the aqueous phase by sulfuric acid followed by extraction with Freon® 113 gave a 9% yield of peroxide assumed to be the peracid $CF_3CF_2CF_2OCF(CF_3)(C=O)OOH$. The results of Example 23 here as well as of Examples 24–40 tracking the effects of power level, ripening time, and surfactant concentration are summarized below.

*These dispersions are not stable without continuous agitation, although it is anticipated that true emulsions could be obtained by exploring other surfactants possibly aided by the addition of small amounts of fluorocarbon fluids such as hexafluoropropylene oxide based oligomers. In order to avoid the hazardous phase separation of a pure peroxide layer, Freon® 113 was added as soon as agitation was stopped.

TABLE 2

Ultrasonic Batch Preparation of HFPOdP as Aqueous Dispersion*
According to Method of Example 23

| Ex. | FC-143 | Ultrasonic Power % | Time | Ripening Time | Dispersion* Yield HFPOdP |
|---|---|---|---|---|---|
| Vary Power to Ultrasonic Horn | | | | | |
| 23 | 0.1 g | 100 | 30 sec | 1 min | 63% |
| 24 | 0.1 g | 80 | 30 sec | 1 min | 62% |
| 25 | 0.1 g | 60 | 30 sec | 1 min | 54% |
| 26 | 0.1 g | 40 | 30 sec | 1 min | 47% |
| 27 | 0.1 g | 20 | 30 sec | 1 min | 12% |
| Vary Ripening Period | | | | | |
| 28 | 0.1 g | 75 | 30 sec | none | 48% |
| 29 | 0.1 g | 75 | 30 sec | 1 min | 55% |
| 30 | 0.1 g | 75 | 30 sec | 3 min | 48% |
| 31 | 0.1 g | 75 | 30 sec | 5 min | 54% |
| 32 | 0.1 g | 75 | 30 sec | 10 min | 50% |
| Vary Level of FC-143 Surfactant | | | | | |
| 35 | none | 100 | 30 sec | 1 min | 30% |
| 36 | 0.05 g | 100 | 30 sec | 1 min | 42% |
| 23 | 0.1 g | 100 | 30 sec | 1 min | 63% |
| 37 | 0.2 g | 100 | 30 sec | 1 min | 55% |
| Vary Period of Ultrasonication and Ripening Period | | | | | |
| 38 | 0.1 g | 75% | 15 sec | none | 55% |
| 39 | 0.1 g | 75% | 30 sec | 3 min | 62% |
| 40 | 0.1 g | 100% | 30 min | none | 49% |

*These dispersions are not stable without continuous agitation. In order to avoid the hazardous phase separation of a pure peroxide layer, Freon ®113 was added as soon as agitation was stopped Clearly it is important that enough power be delivered to the ultrasonic horn and that enough surfactant be present. It is interesting that one can achieve modest 30% conversions of HFPO dimer acid fluoride to peroxide in the absence of both organic solvent and emulsifying agent. Varying the ripening period from 0 to 10 minutes or changing the period of ultrasonic mixing from 15 sec to 30 minutes had only minor effects on yield: thus, dispersions of HFPOdP are surprisingly stable hydrolytically, HFPOdP in water dispersion possibly having a hydrolytic half-life on the order of hours.

Initiation of TFE Polymerization with Aqueous HFPOdP

A 500 ml polymerization kettle loaded with 1 g of ammonium perfluorooctanoate surfactant and 100 ml of water was prechilled on ice.

In Example 40, above, a 5 ml sample of dispersion was withdrawn 30 seconds into the period of ultrasonification. This dispersion sample was immediately added to the polymer kettle. The kettle was sealed, repeatedly pressured with argon and evacuated, and then filled to 67 psi with tetrafluoroethylene from a 1 liter cylinder containing ~33 g of tetrafluoroethylene. This mixture was heated to 37–41° C. After 2 to 3 hours, the polymeric product was recovered by filtration, washed 3× with 1:1 methanol:water, and dried under vacuum giving 11.8 g of poly(tetrafluoroethylene).

Example 41
Batch Stator/Rotor Preparation of HFPOdP in Freon® E1

The contents of a Waring blender cup loaded with 3.95 g of potassium hydroxide pellets (0.06 mole) dissolved in 28 ml of water, 78 ml of Freon® E1, and 6.13 ml of 30% hydrogen peroxide (0.06 mole) were stirred for 10 seconds. Then 7.4 ml of HFPO dimer acid fluoride (0.0352 mole) dissolved in 13 ml of Freon® E2 was poured in as a single charge. The mixture was stirred at "LO" speed for 30 seconds. The organic layer was separated and washed twice with 50 ml of ~5% sodium bicarbonate, giving 77 ml of 0.168 M HFPOdP solution (74% yield). The yield of HFPOdP decreased to 55% with a 10 seconds reaction time and to 47% with a 5 second reaction time.

Example 42
Batch Stator/Rotor Preparation of HFPOdP in Freon® E2

The contents of a Waring blender cup loaded with 3.96 g of potassium hydroxide pellets (0.06 mole) dissolved in 28 ml of water, 169 ml of Freon® E2, and 6.14 ml of 30% hydrogen peroxide (0.06 mole) were stirred for 10 seconds. Then 3.7 ml of HFPO dimer acid fluoride (0.0176 mole) dissolved in 13 ml of Freon® E1 was poured in as a single charge. The mixture was stirred at "LO" speed for 15 seconds. The organic layer was separated and washed twice with 56 ml of ~5% sodium bicarbonate, giving 184 ml of 0.037 M HFPOdP solution (78% yield). The yield of HFPOdP decreased to 74% with a 5 second reaction time.

Example 43
Ultrasonic Batch Preparation of DAEP in Freon® E1

An ice chilled beaker was loaded with 1.5 g of KOH pellets (0.022 mole) dissolved in 5 ml of water, 78 ml of Freon® E1, 2.35 ml of 30% aqueous hydrogen peroxide (0.023 mole), and 5.5 ml of DAE (~0.019 mole). A titanium horn attached to a 40 Khz, 150 watt Dukane ultrasonic power source was immersed roughly halfway down into the pool of reactants. The ultrasonic source was turned on for 30 seconds at full power. The layers were then separated and washed twice with 50 ml of ~5% aqueous sodium bicarbonate. This gave 75 ml of 0.086 M DAEP in Freon® E1 (68% yield based on starting DAE). A DAEP solution passed over Drierite® (anhydrous calcium sulfate), was transferred to a 20° C. water bath, and samples withdrawn over time for iodometric titration. At 20° C., DAEP decomposed with a rate of $\sim 9 \times 10^5$ $sec^{-1}$ (a half-life of 2.2 hours).

Use of DAEP to Initiate Polymerization

A 500 ml polymerization kettle was loaded with 100 ml of Freon® 113 and chilled on wet ice. Once cold, 5.0 ml of a solution 0.086 M in DAEP peroxide was added. The kettle was flushed 5× with argon, once with 5 psi of TFE, and then fed with TFE from a one liter cylinder containing ~33 g of TFE. Over the next two hours TFE pressure in the kettle dropped from 47 to 32 psi with temperature going through a maximum of 44° C. Solid polymer was isolated by filtration, washed 2× with Freon® 113, and dried giving 13.6 g. At 372° C. the melt index with a 15 kg weight was 0.08 g/min. Infrared analysis of cold pressed films found what was likely a —COOCH$_3$ band at 1790 cm$^{-1}$.

Example 44A
Ultrasonic Batch Preparation of MAEP in Freon® E1

An ice chilled beaker was loaded with 3.0 g of KOH pellets (0.044 mole) dissolved in 5 ml of water, 78 ml of Freon® E1, 4.7 ml of 30% aqueous hydrogen peroxide (0.046 mole), and 3.9 ml of MAE (~0.019 mole). A titanium horn attached to a 40 Khz, 150 watt Dukane ultrasonic power source was immersed roughly halfway down into the pool of reactants. The ultrasonic source was turned on for 30 seconds at full power. The layers were then separated and washed twice with 50 ml of ~5% aqueous sodium bicarbonate. This gave 73 ml of 0.089 M MAEP in Freon® E1 (68% yield based on starting MAE). This solution was transferred to a 20° C. water bath and 5.0 ml samples periodically withdrawn for iodometric titration. At 20° C. the peroxide decomposed at a rate of ~8×10$^{-5}$ sec$^{-1}$ (a half-life of ~2.4 hrs). If prior to the kinetic measurements the MAEP solution is passed through Drierite® (anhydrous calcium sulfate) to remove the last bits of water, then the rate comes out ~9×10$^{-5}$ sec$^{-1}$, within experimental error.

Example 44B
Ultrasonic Batch Preparation of SFP

An ice chilled beaker was loaded with 1.5 g of KOH pellets (0.022 mole) and 0.05 g of ammonium perfluorooctanoate dissolved in 5 ml of water, 78 ml of Freon® E1, 2.35 ml of 30% aqueous hydrogen peroxide (0.023 mole), and 6.5 ml of SF (~0.019 mole). A titanium horn attached to a 40 Khz, 150 watt Dukane ultrasonic power source was immersed roughly halfway down into the pool of reactants. The ultrasonic source was turned on for 30 seconds at full power. The layers were then separated and washed twice with 50 ml of ~5% aqueous sodium bicarbonate. This gave 75 ml of 0.083 M SFP in Freon® E1 (~66% yield based on starting SF). A SFP solution passed over Drierite® (anhydrous calcium sulfate), was transferred to a 20° C. water bath, and samples withdrawn over time for iodometric titration. At 20° C., SFP decomposed with a rate of ~7×10$^{-5}$ sec$^{-1}$ (a half-life of 2.9 hours).

In the absence of ammonium perfluorooctanoate yield was 54%. In the absence of ammonium perfluorooctanoate and using Freon® 113 as solvent, yield was 61%.

Use of SFP to Initiate Polymerization

A 500 ml polymerization kettle was loaded with 100 ml of Freon® 113 and chilled on wet ice. Once cold, 5.0 ml of a solution 0.06 M in SFP peroxide was added. The kettle was flushed 5× with argon, once with 5 psi of TFE, and then fed with TFE from a one liter cylinder originally containing ~33 g of TFE. Over the next 1 to 2 hours TFE pressure in the kettle dropped from 49 to 30 psi with temperature going through a maximum of 52° C. Solid polymer was isolated by filtration, washed 3× with Freon® 113, and dried giving 14.0 g. At 372° C. a melt index experiment with a 15 kg weight gave no flow. Cold pressed polymer films showed IR bands at 1470 cm$^{-1}$ consistent with the presence of —SO$_2$F groups.

Use of SFP to Functionalize Benzene

A 200 ml r.b. flask at −25° C. was charged with 140 ml of 0.07 M SFP (9.8 mmoles SFP) in Freon® E1. Using a vacuum pump, the solution was evaporated down to ~40 ml while controlling its temperature to −15 to −30° C. While at −30° C., 10 ml of deoxygenated benzene (112 mmoles) was added by syringe. The mixture was gradually warmed to room temperature (~25° C.) and stirred for several days under nitrogen. Evaporating down gave 9.97 g of yellow fluid. GC/MS showed two major peaks, 30 area percent $(C_6H_5)CF(CF_3)OCF_2CF(CF_3)OCF_2CF_2SO_2F$ (exact mass 541.943674 versus a calculated mass of 541.9669039) and a second unidentified material.

Radical Dimer from SFP

A beaker was loaded with 3 g of KOH (44 mmoles) pellets dissolved in 10 ml water, 4.7 ml of 30% aqueous hydrogen peroxide (46 mmoles), and 150 ml of Freon® 113 with ice bath cooling. Immediately upon addition of 13 ml of SF (~38 mmoles), the mixture was ultrasonicated for 30 seconds using the maximum power output from a titanium horn attached to a 40 Khz, 150 watt Dukane ultrasonic power source. The organic layer was separated, washed 2×50 ml of 5% aqueous sodium bicarbonate and dried by passing through 25 g of Drierite® (anhydrous calcium sulfate pellets). Four such runs were combined and found to be 0.081 M in SFP by iodometric titration. The product was then allowed to stand for four days at room temperature in a r.b. flask under a positive pressure of nitrogen. As a safety precaution the mixture was refluxed for 6 hours, washed with acidic aqueous KI and then aqueous sodium bisulfite. The organic phase was dried and then stripped down to 50.82 g of milky fluid on a rotary evaporator. Vacuum distillation gave 25.47 g of water white oil b$_{0.05}$=83° C. Gas chromatography found a major 74% component that by chemical ionization mass spectroscopy showed aparent—F peak at 910.86 (Calc 910.8571) corresponding to the radical dimer shown below:

Example 45
Ultrasonic Batch Preparation of 7HP

An ice chilled beaker was loaded with 1.5 g of KOH pellets (0.022 mole) dissolved in 5 ml of water, 78 ml of Freon® E1, 2.35 ml of 30% aqueous hydrogen peroxide (0.023 mole), and 4.1 ml of 7HCl (~0.020 mole). A titanium horn attached to a 40 Khz, 150 watt Dukane ultrasonic power source was immersed roughly halfway down into the pool of reactants. The ultrasonic source was turned on for 30 seconds at full power. The layers were then separated. This gave 75 ml of ~0.10 M peroxide in Freon® E1 for a 77% yield.

Use of 7HP to Initiate Polymerization

A 500 ml polymerization kettle was loaded with 100 ml of Freon® 113 and chilled on wet ice. Once cold, 5.0 ml of the 0.1 M peroxide solution prepared in Example 45 was added. The kettle was flushed 5× with argon, once with 5 psi of TFE, and then fed with TFE from a one liter cylinder originally containing ~33 g of TFE. Over the next ~2 hours TFE pressure in the kettle dropped from 60 to 30 psi with temperature going through a maximum of 58° C. Solid polymer was isolated by filtration, washed 3× with Freon® 113, and dried giving 14.2 g. At 372° C. the melt index with a 15 kg weight gave a flow of 0.04 g/min. The polymer had an infrared adsorption at 3006 cm$^{-1}$ consistent with the presence of —CF$_2$H end groups.

Example 46
Ultrasonic Batch Preparation of BrP

An ice chilled beaker was loaded with 1.5 g of KOH pellets (0.022 mole) dissolved in 5 ml of water, 78 ml of Freon® E1, 2.35 ml of 30% aqueous hydrogen peroxide (0.023 mole), and 9.2 ml of 75% pure BrCl (~0.023 mole). A titanium horn attached to a 40 Khz, 150 watt Dukane ultrasonic power source was immersed roughly halfway down into the pool of reactants. The ultrasonic source was turned on for 30 seconds at full power. The layers were then separated and washed twice with 50 ml of ~5% aqueous sodium bicarbonate. This gave 74 ml of 0.10 M BrP in Freon® E1 (~64% yield based on starting BrCl).

Use of BrP to Initiate Polymerization

A 500 ml polymerization kettle was loaded with 100 ml of Freon® 113 and 5.0 ml of a solution ~0.1 M in BrP peroxide. The kettle was flushed 5× with argon, once with 5 psi of TFE, and then fed with TFE from a one liter cylinder originally containing ~33 g of TFE. Over the next ~2 hours TFE pressure in the kettle dropped from 54 to 25 psi with temperature going through a maximum of 54° C. Solid polymer was isolated by filtration, washed 3× with Freon® 113, and dried giving 20.6 g. At 372° C. the melt index with a 15 kg weight gave a flow of 0.09 g/min.

Example 47
Ultrasonic Batch Preparation of IP

An ice chilled beaker was loaded with 1.5 g of KOH pellets (0.022 mole) dissolved in 5 ml of water, 78 ml of Freon® E1, 2.35 ml of 30% aqueous hydrogen peroxide (0.023 mole), and 1.5 ml (3.04 g=11 mmoles) of IF. A titanium horn attached to a 40 Khz, 150 watt Dukane ultrasonic power source was immersed roughly halfway down into the pool of reactants. The ultrasonic source was turned on for 30 seconds at fall power. The layers were then separated and washed twice with 50 ml of ~5% aqueous sodium bicarbonate. This gave 72 ml of 0.022 M IP in Freon® E1 (~29% yield based on starting IF). Even though this initiator was stored in a −15° C. refrigerator insoluble iodine crystals were soon visually apparent. Iodine substituted peroxides appear quite unstable and should be handled with caution. On-demand, continuous methods of making peroxide may be a particularly safe and effective way to make and use iodinated peroxides.

Use of IP to Initiate Polymerization

A 500 ml polymerization kettle was loaded with 100 ml of Freon® 113 and 20 ml of a solution ~0.022 M in IP peroxide. The kettle was flushed 10× with argon, twice with 5 psi of TFE, and then fed with TFE from a one liter cylinder originally containing ~33 g of TFE. Over the next ~2 hours TFE pressure in the kettle dropped from 58 to 38 psi with temperature going through a maximum of 40° C. Solid polymer was isolated by filtration, washed 3× with Freon® 113, and dried giving 9.5 g. At 372° C. the melt index with a 5 kg weight gave a flow of 2 g/min, the extrudate being a strong pink from released iodine.

Example 48
Ultrasonic Batch Preparation of PhenoxyP

An ice chilled beaker was loaded with 1.5 g of KOH pellets (0.022 mole) dissolved in 5 ml of water, 0.05 g ammonium perfluorooctanoate, 2.35 ml of 30% aqueous hydrogen peroxide (0.023 mole), and 5.29 g of Phenoxy-COF (10.7 mmoles) dissolved in 100 ml of Freon® E1. A titanium horn attached to a 40 Khz, 150 watt Dukane ultrasonic power source was immersed roughly halfway down into the pool of reactants. The ultrasonic source was turned on for 30 seconds at full power. The layers were then separated and washed twice with 50 ml of ~5% aqueous sodium bicarbonate. The organic phase was washed through 25 g of Drierite® (anhydrous calcium sulfate) with an additional 25 ml of Freon® E1. This gave 115 ml of 0.05 M PhenoxyP in Freon® E1 (~100% yield based on starting PhenoxyCOF).

Use of PhenoxyP to Initiate Polymerization

A 500 ml polymerization kettle was loaded with 100 ml of Freon® 113 and 20 ml of ~0.05 M in PhenoxyP in Freon® E1. The kettle was flushed 10× with argon, twice with 5 psi of TFE, and then fed with TFE from a one liter cylinder originally containing ~33 g of TFE. The reaction mixture exothermed from 20 to 59° C. going through a maximum pressure of 60 psi finally ending up at 31 psi at 28° C. ~4 hours later. Solid polymer was isolated by filtration, washed 3× with Freon® 113, and dried, 15.42 g. At 372° C. with a 15 kg weight in a melt index apparatus no flow was observed.

Example 49
Ultrasonic Batch Preparation IBP in Hexane

A. Using tetrabutylammonium hydroxide as base: A beaker was loaded with 27.8 ml of 40% aqueous tetra-n-butylanmuonium hydroxide (40 mmoles), 4.1 ml of 30% hydrogen peroxide (40 mmoles), and 100 ml hexane with chilling and stirring. After adding 3.15 ml of isobutyryl chloride (30 mmoles) the mixture was ultrasonicated at maximum power for 30 seconds using an ultrasonic horn connected to a 40 Khz, 150 watt Dukane power source. The organic layer was separated and washed twice with 50 ml of 5% aqueous $NaHCO_3$ giving 95 ml of organic phase that was found to be 0.074 M in peroxide by iodometric titration for an overall yield of 47% based on starting isobutyryl chloride.

B. Using potassium hydroxide as base: Dissolve 3.96 g of 85% KOH (60 mmoles) in 6.13 ml of 30% hydrogen peroxide (60 mmoles) with ice bath cooling in a beaker. Add 90 ml of hexane and 3.15 ml of isobutyryl chloride (30 mmoles). An ultrasonic horn connected to a 40 Khz, 150 watt Dukane power source was started up at ~75% of maximum power and lowered into the reaction mixture. After 1 minute, ultrasonication was stopped. The organic layer separated immediately and was washed twice with 50 ml of 5% aqueous $NaHCO_3$. The organic layer had a total volume of 90 ml and was found to be 0.049 M in IBP by iodometric titration for an overall yield of 29% based on starting isobutyryl chloride.

Example 50
Ultrasonic Batch Preparation 5PDC in Freon® E1

A beaker was loaded with 0.92 g of lithium hydroxide monohydrate (22 mmoles) and 0.05 g ammonium perfluorooctanoate dissolved in 10 ml of water. Once solution was complete and the mixture had been chilled with an ice bath, 2.2 ml of 30% hydrogen peroxide (22 mmoles), 75 ml of Freon® E1, and 2.5 ml of 94% pure 5Cl (~13 mmoles) were added. An ultrasonic horn connected to a 40 Khz, 150 watt Dukane power source was started up at ~75% of maximum power and lowered into the reaction mixture. After 25 seconds, ultrasonication was stopped. The organic layer was washed twice with 50 ml of 5% aqueous $NaHCO_3$. The organic layer had a total volume of 73 ml and was found to be 0.034 M in 5PDC by iodometric titration for an overall yield of 38% based on starting 5Cl.

Example 51
Continuous Reactor Preparation of EtHDC in Freon® E1 Mixing T Followed by Ultrasonic Mixer Syringe pump (3), loaded with 15% by weight aqueous $H_2O_2$, was started up at 0.659 ml/min. Syringe pump (2), loaded with 24% by weight aqueous KOH, was started up at 0.744 ml/min. Syringe pump (1), loaded with 0.255 M 2-ethylhexyl chloroformate in Freon® E1, was started up at 3.396 ml/min. The streams from the three pumps, held at 20° C. by a surrounding water bath, were joined into a single stream at a ⅛th" union cross Hoke® fitting (4). The ratio of reactants at this point was 3.5 moles of $H_2O_2$: 4.5 moles of KOH: 1 mole of 2-ethylhexyl chloroformate, making for an 7 fold excess of $H_2O_2$ and a 4.5 fold excess of KOH over 2-ethylhexyl chloroformate in terms of reaction stoichiometry. Immediately after exiting union cross (4), the liquid stream was run via an 0.035" I.D. line of ~0.1 ml volume into the bottom cup of the 1.6 ml ultrasonic reactor cavity (5) also chilled with wet ice. The power source to the ⅜" diameter ultrasonic horn (6) was turned on at 50% of full scale, providing ~15 watts of power to the ultrasonic cavity. Product exited as a stream at the top of the ultrasonic cavity at 22° C. with an average residence time in the cavity of 20 seconds. The reactor was run for several minutes to flush out the lines and achieve steady operating conditions, this foreshot being run into waste poly container (7). The reactant stream was then diverted to sampling container (8) already containing 100 ml of 2% aqueous $NaHCO_3$. The organic layer was separated and washed twice with 75 ml of 5% aqueous sodium bicarbonate. This gave 38 ml of 0.126 M ETHDC in Freon® E1 for a 91.8% yield based on starting 2-ethylhexyl chloroformate and in a duplicate run 39 ml of 0.121 M ETHDC in Freon® E1 for a 90.4% yield.

Increasing flow rates so as to obtain a 15 second residence time gave a yield of 76% and increasing flow rates still further to obtain a 10 second residence time gave a 66% yield of ETHDC. Replacing the ultrasonic mixer with a jet mixer of 0.086 ml volume and running at 190 ml total flow/min (a nominal residence time of 0.027 sec) reduced ETHDC yield still further to 9.3%.

Example 52
Ultrasonic Batch Preparation of t-Butylperacetate in Hexane

A. Potassium hydroxide as base: A beaker was loaded with 1.23 g ~85% KOH pellets (19 mmoles) dissolved up to 15.9 ml with water, 5.4 ml of 70% aqueous t-butylhydroperoxide (40 mmoles), 100 ml of hexane, and 1.4 ml of acetyl chloride (20 mmoles) with ice bath cooling. An ultrasonic horn connected to a 40 Khz, 150 watt Dukane power source was started up at maximum power and lowered into the reaction mixture. After 25 seconds, ultrasonication was stopped, the organic layer separated and washed twice with 50 ml of 5% aqueous $NaHCO_3$. The organic layer had a total volume of 100 ml and was found to be 0.082 M in peroxide by iodometric titration for an overall yield of 41% based on starting acetyl chloride.

B. Using 10% excess potassium hydroxide as base and tetra-n-butyl-ammonium perchlorate as phase transfer catalyst: A beaker was loaded with 1.23 g ~85% KOH pellets (19 mmoles) and 0.1 g of tetra-n-butylammonium perchlorate dissolved up to 15.9 ml with water, 5.4 ml of 70% aqueous t-butylhydroperoxide (40 mmoles), 100 ml of hexane, and 1.4 ml of acetyl chloride (20 mmoles) with ice bath cooling. An ultrasonic horn connected to a 40 Khz, 150 watt Dukane power source was started up at maximum power and lowered into the reaction mixture. After 25 seconds, ultrasonication was stopped, the organic layer separated and washed twice with 50 ml of 5% aqueous $NaHCO_3$. The organic layer had a total volume of 100 ml and was found to be 0.11 M in peroxide by iodometric titration for an overall yield of 55% based on starting acetyl chloride.

Example 53
Ultrasonic Batch Reaction of Benzoyl Chloride

A. Giving Benzoyl Peroxide as Major Product: A beaker was loaded with 1.23 g ~85% KOH pellets (19 mmoles) dissolved up to 15.9 ml with water, 2.04 ml of 30% aqueous hydrogen peroxide (20 inmoles), 50 ml of Freon® E1, and 2.32 ml of benzoyl chloride (20 mmoles) with ice bath cooling. An ultrasonic horn connected to a 40 Khz, 150 watt Dukane power source was started up at maximum power and lowered into the reaction mixture. After 25 seconds, ultrasonication was stopped, the solids filtered off, washed with water, and sucked dry on the filter. This gave 1.52 g of white solid, a 63% yield of benzoyl peroxide based on starting benzoyl chloride. The filtrate was brought to pH ~1 by the addition of concentrated sulfuric acid and then extracted three times with methylene chloride. The three methylene chloride extracts had a combined volume of 80 ml, 10.0 ml of which took 0.2 ml of 0.1 N thiosulfate in iodometric peroxide titration. The failure to find significant amounts of peroxide in the methylene chloride extracts indicates that little if any benzoyl hydroperoxide $[C_6H_5(C=O)OOH]$ was formed during the reaction.

B. Giving Perbenzoic Acid (Benzoyl Hydroperoxide) as Major Product

A beaker was loaded with 50 ml of 30% hydrogen peroxide, 3.42 ml of 45% aqueous KOH (40 mmoles), and 0.2 ml of 40% aqueous tetrabutylammonium hydroxide, the mixture being made cautiously with ice bath cooling and stirring. An ultrasonic horn connected to a 40 Khz, 150 watt Dukane power source was started up at maximum power and lowered into the reaction mixture. Then 2.32 ml of benzoyl chloride (20 mmoles) were added and after 15 seconds of ultrasonic agitation the horn was turned off. Trace solids, 0.08 g, were filtered off. The filtrate was immediately added cautiously to an ice cold mixture of 5 ml of concentrated sulfuiric acid+45 ml of water+25 ml of methylene chloride. The methylene chloride layer was separated and combined with two subsequent 25 ml extracts. This gave 75 ml of methylene chloride solution, 5.0 ml of which took 9.1 ml of 0.1 N thiosulfate in iodometric titration, a 34% yield based on starting benzoyl chloride assuming the product to be $[C_6H_5(C=O)OOH]$.

Example 54
Ultrasonic Batch Preparation of Trichloroacetyl Peroxide

A. Potassium Hydroxide as Base. A beaker was loaded with 1.98 g of KOH pellets (30 mmoles), 28 ml of water, 90 ml of Freon® 113, 3.07 ml of 30% aqueous hydrogen peroxide, and finally 1.9 ml of trichioroacetyl chloride (17 mmoles) with ice bath cooling. An ultrasonic horn connected to a 40 Khz, 150 watt Dukane power source was immediately started up at 75% maximum power and lowered into the reaction mixture. After 15 seconds, the ultrasonic horn was turned off and the reaction mixture poured into a prechilled 250 ml Erlenmeyer flask sitting on dry ice. The reaction mixture was first allowed to freeze solid and then warmed with swirling. As soon as the Freon® 113 phase had thawed entirely to 87 ml of fluid, a 5.0 ml sample was drawn and found to take 6.0 ml of 0.1 N sodium thiosulfate in iodometric titration (yield 61% based on starting trichloroacetyl chloride). In a control experiment, the synthesis was repeated except that the trichloroacetyl chloride was omitted from the reactants. In this case peroxide titration of the freshly thawed Freon® 113 layer took but 0.1 ml of 0.1 N sodium thiosulfate. It should be noted that trichloroacetyl peroxide is sufficiently unstable that a typical work up—separating the organic phase and washing twice with 5% aqueous sodium bicarbonate—gave but a 9% yield in an otherwise identical synthesis.

The method described here avoids the inconveniently low temperatures, 1 hour reaction times, and hazardous isolation features of prior work with trichloroacetyl peroxide (See U.S. Pat. No. 2,580,373) something likely to apply to other unstable peroxides. Being able to make a highly unstable peroxide and deliver it to a reactor all in a matter of seconds makes the use of such peroxides much more practical on an industrial scale. The reported half-life of trichloroacetyl peroxide is ~0.6 hr at 2° C.

B. Lithium Hydroxide as Base. A beaker was loaded with 1.25 g of lithium hydroxide monohydrate (30 mmoles), 28 ml of water, 90 ml of Freon® 113, 3.07 ml of 30% aqueous hydrogen peroxide, and finally 1.9 ml of trichloroacetyl chloride (17 mmoles) with ice bath cooling. An ultrasonic horn connected to a 40 Khz, 150 watt Dukane power source was immediately started up at 75% maximum power and lowered into the reaction mixture. After 15 seconds, the ultrasonic horn was turned off and the reaction mixture poured into a prechilled 250 ml Erlenmeyer flask sitting on dry ice. The reaction mixture was first allowed to freeze solid and then warmed with swirling. As soon as the Freon® 113 phase had thawed entirely to 88 ml of fluid, a 5.0 ml sample was drawn and found to take 6.2 ml of 0.1 N sodium thiosulfate in iodometric titration (yield 64% based on starting trichloroacetyl chloride).

Example 55
Ultrasonic Batch Preparation of 5P

A beaker was loaded with 2.5 g of lithium hydroxide monohydrate (60 mmoles), 28 ml of water, 0.1 g of ammonium perfluorooctanoate, and 90 ml of Freon® E1 with ice bath cooling. Once solution was complete, 6.13 ml of 30% hydrogen peroxide (60 mmoles) were added with stirring. The solution was chilled again to ~0° C. and then 3.5 ml of 5COF (18.7 mmoles) were added. An ultrasonic horn connected to a 40 Khz, 150 watt Dukane power source was started up at ~50% of maximum power and lowered into the reaction mixture. After 15 seconds, ultrasonication was stopped, the aqueous phase frozen on dry ice, and then 5.0 ml of the organic layer withdrawn for peroxide titration. The organic layer was found to be 0.01 M in 5P for an yield of ~10%.

Example 56
Ultrasonic Batch Preparation of $CF_3CF_2CF_2OCF(CF_3)(C=O)OOC(CH_3)_3$ Example of mixed fluorocarbon/hydrocarbon structure A beaker was loaded with 1.23 g potassium hydroxide pellets (19 mmoles), 15 mL water, 100 mL Freon® 113, 0.1 g of tetrabutylammonium perchlorate, and 5.4 mL of 70% aqueous t-butylhydroperoxide with ice bath cooling. With continued ice bath cooling, 4.0 mL of HFPOCOF (20 mmoles) were added. An ultrasonic horn connected to a 40 khz, 150 watt Dukane power source was immediately started up at 75% maximum power and lowered into the reaction mixture. After 25 seconds the horn was turned off. The organic phase was separated and washed twice with 50 mL of 5% aqueous sodium bicarbonate. This gave 100 mL of organic phase, 5.0 mL of which took 7.2 mL of 0.1 N thiosulfate in iodometric titration for peroxide (36% yield). This peroxide was found to have a half-life of ~5 hours at 0° C.

Example 57
Ultrasonic Batch Preparation of Dichloroacetyl Peroxide

A beaker was loaded with 1.25 g of lithium hydroxide monohydrate (30 mmoles), 28 mL of water, 90 mL of Freon® 113, 3.07 mL of 30% aqueous hydrogen peroxide (30 mmoles), and finally 1.64 mL of dichloroacetyl chloride (17 mmoles) with ice bath cooling. An ultrasonic horn connected to a 40 Khz, 150 watt Dukane power source was immediately started up at 75% maximum power and lowered into the reaction mixture. After 15 seconds, the ultrasonic horn was turned off and the reaction mixture poured into a prechilled 250 mL Erlemneyer flask sitting on dry ice. The reaction mixture was first allowed to freeze solid and then warmed with swirling. As soon as the Freon® 113 phase has thawed entirely to 90 mL of fluid, a 5.0 mL sample was drawn and found to take 4.5 mL of 0.1 N sodium thiosulfate in iodometric titration (yield 48% based on starting dichloroacetyl chloride).

Example 58
Ultrasonic Batch Prep. of HFPOdP
Example of Low Water Content Reaction Mixture
Example of Work-up not Requiring Phase Separation A beaker loaded with 78 mL Freon® E1, 1.0 mL 30% hydrogen peroxide (10 mmoles), and 2.1 mL of HFPOCOF (10 mmoles) was chilled in an ice bath. Finally 0.86 mL of 45 wt % aqueous KOH was added (10 mmoles). An ultrasonic horn connected to a 40 khz, 150 watt Dukane power source was immediately started up at maximum power and lowered into the reaction mixture. After 25 seconds the horn was turned off. This gave a white, opaque organic phase with a few droplets of water visibly floating up top. Using an additional 10 mL of Freon® E1, the reaction mixture was washed through a chromatography column precharged with 50 g of Drierite® (anhydrous $CaSO_4$ pellets) and 25 mL of Freon® E1. A period of 2 to 3 minutes was allowed for the reacton mixture to wash through the Drierite®. This gave 100 mL of slightly hazy Freon® E1 solution, 5.0 mL of which took 3.5 mL of 0.1 N thiosulfate in iodometric peroxide titration (70% yield based on starting HFPOCOF). Even after washing this organic phase twice with 50 mL of 5% aqueous sodium bicarbonate, it still took 3.5 mL of 0.1 N thiosulfate in peroxide titration, indicating that unreacted or excess hydrogen peroxide did not make it past the Drierite®.

In many other examples herein the product is worked up by mechanically separating the water phase from the organic phase that contains the peroxide. The organic layer that has been separated can then be washed and, if anhydrous solution is needed, passed through a bed of desiccant. Example 58 here demonstrates an alternative work-up giving dry initiator solution free of hydrogen peroxide contaminant: if the original peroxide synthesis is run with minimal water as in the example here, the mechanical separation and washing steps can be omitted entirely, the reaction mixture going instead directly through a dessicant bed. This could be of particular value in constructing small, portable peroxide generation units.

Example 59
Ultrasonic Batch Preparation of
${CF_3CF_2CF_2O[CF(CF_3)CF_2O]_{6.3}CF(CF_3)(C=O)}_{-2}$
Example of high MW peroxide
Example of low water content reaction mixture
Example of work-up not requiring phase separation
Example using an oligomeric mix A beaker loaded with 78 mL Freon° E1, 2.04 mL 30% hydrogen peroxide (20 mmoles) and 8.5 mL $CF_3C_2CF_2O$

[CF(CF$_3$)CF$_2$O]$_{6.3}$CF(CF$_3$)(C=O)F (~10 mmoles, MW=~1300) was chilled in an ice bath. Finally 1.00 mL of 45 wt % aqueous KOH (12 mmoles) was added. An ultrasonic horn connected to a 40 khz, 150 watt Dukane power source was immediately started up at maximum power and lowered into the reaction mixture. After 15 seconds the horn was turned off. This gave a viscous white emulsion. Washing the emulsion through 50 g of Drierite® (anhydrous CaSO$_4$ pellets) in a chromatography column with an additional 25 mL of Freon® E1 gave 80 mL of hazy Freon® E1 solution, 5.0 mL of which took 3.9 mL of 0.1 N thiosulfate in iodometric peroxide titration, a 62% yield of {CF$_3$CF$_2$CF$_2$O[CF(CF$_3$)CF$_2$O]$_{6.3}$CF(CF$_3$)(C=O)}$_{-2}$. This procedure keeps the volume of water small so that passage through a drying agent is practical and avoids a layer separation step that would be made difficult by the emulsion (see below).

As an example of how difficult layer separations can become when making high molecular weight peroxides, a beaker was loaded with 3.01 g KOH pellets dissolved in 10 mL water, 78 mL Freon® E1, and 4.70 mL 30% hydrogen peroxide with ice bath cooling. After adding 8.5 mL of CF$_3$CF$_2$CF$_2$O[CF(CF$_3$)CF$_2$O]$_{6.3}$C(CF$_3$)(C=O)F, the reaction mixture was ultrasonicated at maximum power with the same 150 watt horn as above for 25 seconds. This gave a viscous, milky-white, single-phase emulsion. Freezing this emulsion on dry ice gave perhaps a bit of a layer separation. Bringing strongly acidic with sulfuric acid produced a milky upper layer, a hazy middle layer, and a gelatinous looking lower layer. Presumably soaps such as CF$_3$CF$_2$CF$_2$O[CF(CF$_3$)CF$_2$O]$_{6.3}$CF(CF$_3$)(C=O)O$^-$K$^+$ are formed as by-products of the peroxide synthesis and may become an increasing problem with increasing molecular weight.

Example 60

Benzoyl Peroxide

Figure 3:
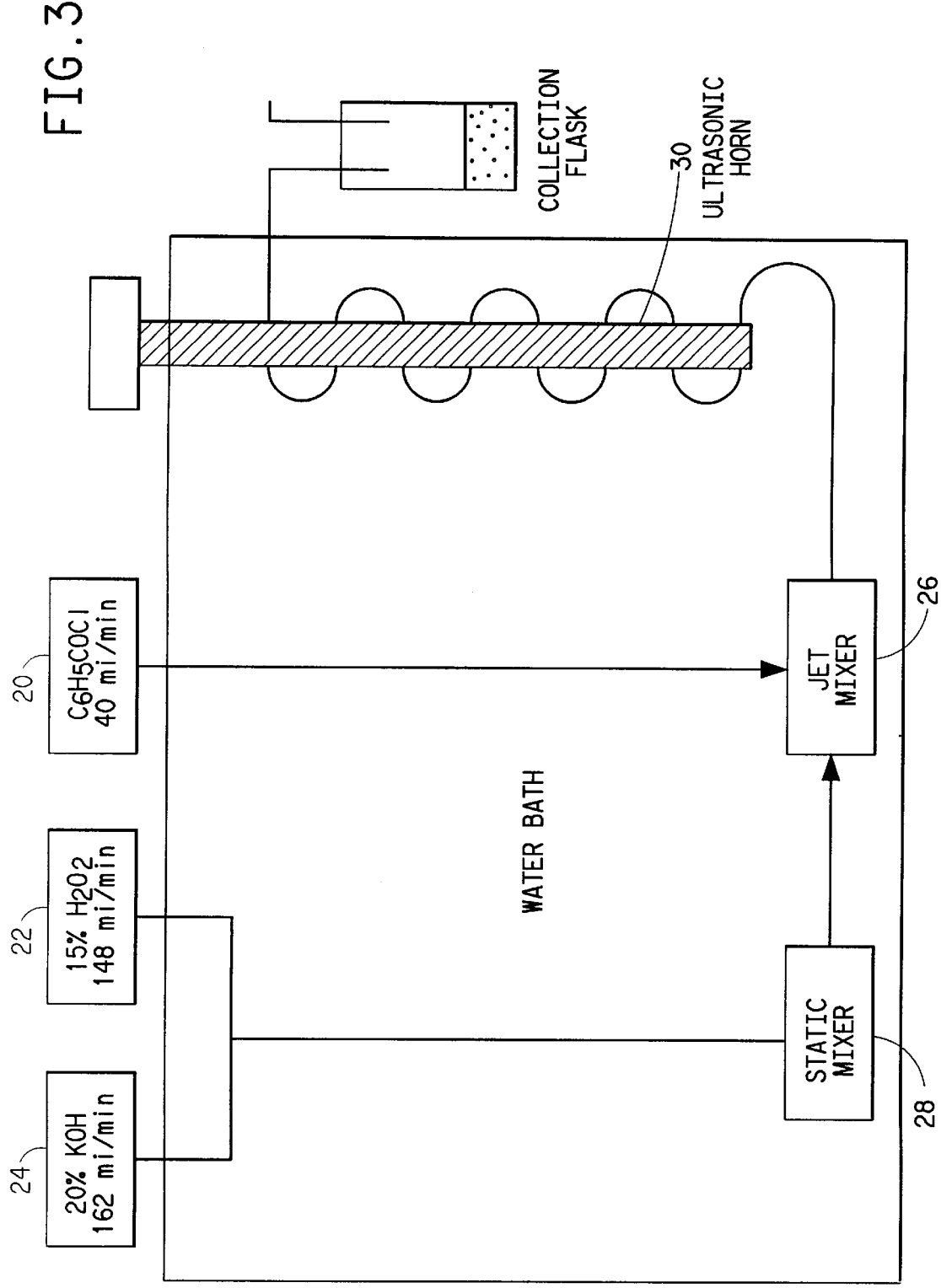
FIG. 3 is a schematic description of a flow reaction system for the continuous jet/ultrasonic embodiment of the process.

A. Jet+Ultrasonic Mixing at 0° C. The three reactants required to make benzoyl peroxide were brought together under conditions of intense mixing in a flow system. See FIG. 3.

Three ISCO syringe pumps were simultaneously started up, the first (20) delivering 40 ml/min of benzoyl chloride, the second (22) delivering 148 ml/min of 15% aqueous hydrogen peroxide, and the third (24) delivering 162 ml/min of 20% aqueous KOH. In terms of the balanced equation for making benzoyl peroxide, this put H$_2$O$_2$ in a 4x stoichiometric excess and KOH in a 2x stoichiometric excess over benzoyl chloride. The KOH and H$_2$O$_2$ streams were combined in a 27 element Kenics mixer (internal volume 1.4 ml, ³⁄₁₆" OD×7.5" long) immediately before being run straight through a ⅛" Hoke® T fitting. In the case of this aqueous stream flow rates were high enough that no orifice was needed, the 0.08" inside diameter of the ⅛" stainless steel tubing running to the Hoke® fitting being adequate. The benzoyl chloride stream was brought in the side arm of the Hoked® T fitting using an 0.02" orifice to increase its velocity. Fluid pressures on the inlet side of the Hoke® T fitting were 38 psi. The high velocity benzoyl chloride stream impinging into the aqueous stream created intense turbulence called jet mixing (26) within the Hoke® T fitting.

Immediately upon leaving the jet mixer/Hoke® fitting (26), the reaction mixture was subjected to an additional about 13 seconds of intense agitation in order to increase reaction time, residence time in the jet mixer/Hoke® fitting being only 0.01–0.02 sec. The transferline connecting the jet mixer/Hoke® fitting to the product collection vessel was essentially wrapped around an ultrasonic horn (30) as described below.

The jet mixer/Hoke® fitting (26) was immersed in a 0° C. water bath along with a 20 KHz 1kw ultrasonic horn (30) measuring 1" in diameter by 24" long. A 190" length of 0.1875" ID Teflon® PFA tubing connecting the jet mixer/Hoke® fitting to the product collection flask was first passed about ½" below the tip of the ultrasonic horn, then spiraled for 166" of its length around the horn, and finally, for its last 24", run out to the product collection flask. At the flow rate in this experiment the residence time in the jet mixer+the 190" of transferline was 15 seconds. The transferline was run to an Erlenmeyer flask containing 200 ml of ice cold toluene dissolving the benzoyl peroxide. Optionally, the toluene can be omitted and the benzoyl peroxide filtered off as solid. Product pulsed out of the transferline as roughly inch long cylinders of self adherent white paste alternating with fluid. As the benzoyl peroxide pulsed out the end of the transferline, pressure immediately following the jet mixer similarly pulsed from about 10–35 psi. Product was collected for 33 seconds. An additional 50 ml of toluene was added to the product collection flask bringing all the benzoyl peroxide into solution. Washing the toluene 2× with 150 ml of 10% aqueous KOH gave 272 ml of toluene solution 0.354 M in benzoyl peroxide by iodometric titration (102% yield).

B. Jet Mixing Alone. The equipment was set up and run much as in part (a) above except flow rates and water bath temperatures were varied. More importantly the ultrasonic horn was never turned on. Results are summarized in the table below.

| Water Bath Temperature | Residence Time | Yield | Appearance |
| --- | --- | --- | --- |
| 0° C. | 15 sec | 54% | Solid in oil |
| 0° C. | 11 sec | 49% | Solid in oil |
| 26° C. | 15 sec | 66% | Solid Paste, pulsed |
| 46° C. | 15 sec | 78% | Solid Paste, pulsed |

Using an optically clear transferline made of Teflon® PFA, visual inspection showed that much of the benzoyl peroxide had formed as a solid by the time that the reaction mixture exited the Hoke® fitting/jet mixer. Minimal optimization improved yields considerably: increasing bath temperature to 26° C. and then to 46° C. increased yields to 66% and 78% respectively.

Example 61

Continuous Reactor Preparation of HFPO Dimer Peroxide in Freon® E2

Use of Gear Pumps Instead of Syringe Pumps

In the continuous examples above syringe pumps were used to deliver the reactants. The experiment here shows that the use of gear pumps gives a similar result. Using the same apparatus and set up as described for Example 11B all three syringe pumps were replaced by gear pumps manufactured by Micro Pump. For the solution of HFPO dimer acid fluoride in Freon® E2 the pump was equipped with a #185-000 head while for the KOH and H$_2$O$_2$ solutions both pumps were equipped with #187-000 heads. All three gear pumps used a Model #7144-00 drive motor from Cole Parmer Instrument Company as controllers. Running much as described for Example 11B gave an 84.3% yield of HFPO dimer peroxide. The run is described in greater detail below.

The same equipment was used as in Example 1 except that the syringe pumps were replaced by gear pumps, the H$_2$O$_2$ and KOH streams were combined prior to mixing with the organic stream, union cross (4) and ultrasonic reactor (5) have been replaced by a jet mixer, and the 0° C. ice bath has been replaced by a 26° C. water bath. The jet mixer was a ⅛" Hoke® T with an internal diameter of 0.094" and an internal length of 0.76", making for an internal volume of 0.086 ml. In these runs the organic phase was pumped straight through the ⅛" Hoke® T at 125 ml/minute. The combined aqueous KOH/$H_2O_2$ phase was pumped into the ⅛" Hoke® T at 84 ml/min via an 0.038" I.D. tube set 90° to the organic flow. Reducing the diameter of the tubing entering the side inlet of the T to 0.038" provides the orifice dimensions required for jet mixing at the flow rates given above and for the viscosities/densities of the fluids.

Gear pump (3), loaded with 12.9% by weight aqueous $H_2O_2$, was started up at 31 ml/min. Gear pump (2), loaded with 18.3% by weight aqueous KOH, was started up at 53 ml/min. Using a 27 element Kenics static mixer, the KOH and $H_2O_2$ streams were combined to a single aqueous stream flowing at 84 ml/min. Gear pump (1), loaded with 5% by weight HFPO dimer acid fluoride in Freon® E2, was started up at 125 ml/min. Using 0.038" I.D. tubing, the combined aqueous stream was passed into the side arm of the Hoke® T at 85.0 ml/min impinging into the organic stream moving straight through the Hoke® T at 125 ml/min. The ratio of reactants at this point was 4 moles of $H_2O_2$: 6.5 moles of KOH: 1 mole of HFPOCOF, making for a large excess of both $H_2O_2$ and KOH over HFPOCOF in terms of reaction stoichiometry. The liquid stream exiting the Hoke® T at 28° C. was run via an 0.085" I.D. line of ~3.3 ml volume to the collection bottle. The 0.085" diameter of the exit line is such that the turbulent flow may persist after the jet mixer, although this was not confirmed by experiment. Average residence time in the reactor was 0.025 seconds considering just the volume of the Hoke® T serving as the jet mixer or 0.97 seconds considering the volume of the jet mixer and the exit lines together. The continuous reactor was run for 2 minutes to flush out the lines and achieve steady operating conditions, this foreshot being run into waste poly container (7). The reactant stream was then diverted to sampling container (8) where 123 ml of organic phase were collected over the next minute for purposes of product analysis. The organic layer was separated and washed twice with 75 ml of 5% aqueous sodium bicarbonate. Iodometric titration found 0.102 M HFPOdP in Freon® E2 for a yield of 84.3% based on starting HFPOCOF.

Example 62
Continuous Reactor Preparation of HFPO Dimer Peroxide in Freon® E2 Jet Mixer The same equipment was used as in Example 11B except that all flow rates were increased and the transferline after the jet mixer was changed from a tube ~3' long by 0.085" in inside diameter to a tube 22.5" long by 0.155" in internal diameter. The jet mixer was as before a ⅛" Hoke® T with an internal diameter of 0.094" and an internal length of 0.76", making for an internal volume of 0.086 ml. In these runs the organic phase was pumped straight through the ⅛" Hoke® T at 250.08 ml/minute. The combined aqueous KOH/$H_2O_2$ phase was pumped into the ⅛" Hoke® T at 168.48 ml/min via an 0.044" I.D. tube set 90° to the organic flow. Reducing the diameter of the tubing entering the side inlet of the T to 0.038" provides the orifice dimensions required for jet mixing at the flow rates given above and for the viscosities/densities of the fluids.

Syringe pump (3), loaded with 12.9% by weight aqueous $H_2O_2$, was started up at 62.3 ml/min. Syringe pump (2), loaded with 18.3% by weight aqueous KOH, was started up at 106 ml/min. Using a 27 element Kenics static mixer, the KOH and $H_2O_2$ streams were combined to a single aqueous stream flowing at 168 ml/min. Syringe pump (1), loaded with 5% by weight HFPO dimer acid fluoride in Freon® E2, was started up at 250 ml/min. Using 0.044" I.D. tubing, the combined aqueous stream was passed into the side arm of the Hoke® T at 168.48 ml/min impinging into the organic stream moving straight through the Hoke® T at 250.08 ml/min. The ratio of reactants at this point was 4 moles of $H_2O_2$: 6.5 moles of KOH: 1 mole of HFPOCOF, making for a large excess of both $H_2O_2$ and KOH over HFPOCOF in terms of reaction stoichiometry. Fluid pressure just before the jet mixer was 7.4 psi and 1.8 psi just after. The liquid stream exiting the Hoke® T at ~30° C. was run via an 0.155" I.D. line of ~7 ml volume to the collection bottle. The 0.155" diameter of the exit line is such that the turbulent flow may persist after the jet mixer, although this was not confirmed by experiment. Average residence time in the reactor was 0.012 seconds considering just the volume of the Hoke® T serving as the jet mixer or 1.02 seconds considering the volume of the jet mixer and the exit lines together. The continuous reactor was run for 1 minute to flush out the lines and achieve steady operating conditions, this foreshot being run into waste poly container (7). The reactant stream was then diverted to sampling container (8) where ~123 ml of organic phase were collected over 30 seconds for purposes of product analysis. The organic layer was separated and washed twice with 75 ml of 5% aqueous sodium bicarbonate. The organic phase titrated 0.115 M in HFPOdP in Freon® E2 for a yield of 94% based on starting HFPOCOF.

Making ~123 ml of 0.115 M HFPOdP in a volume of 0.086 ml in 30 seconds corresponds to a productivity of 108,000 lbs of HFPOdP/gallon/hr. The fastest comparable prior art we are aware of, U.S. Pat. No. 2,792,423, reports making 7.2 g of 4P/100 ml/min for a productivity of 36 lbs of 4P/gallon/hr. Putting this in the language of Attachment 3, a productivity of 36 lbs of 4P/gal/hr is equal to ~1200 g of active oxygen content/gal/hr and a productivity of 108,000 lbs of HFPOdP/gal/hr is equal to 2,380,000 g of active oxygen content/gal/hr. Underestimating our productivity by treating both the jet mixer and the transfer line as the reactor, we conservatively estimate this example makes HFPOdP at >1300 LBS/gallon/hr and equivalent active oxygen content at >29,000 g/gal/hr.

Example 63
Continuous Reactor Preparation of HFPO Dimer Peroxide in Freon® E2 Mini Jet Mixer The equipment described in Example 62 makes enough HFPO dimer peroxide to run a large commercial-scale polymerization facility. For purposes of running small portable processes or of coupling our peroxide generator to a polymerization pilot plant, the volume of product produced in Example 62 can be scaled down at least 20 to 200×.

Much the same equipment was used as in Example 11B except that all flow rates were decreased, orifice diameters were decreased in the jet mixer, and the transferline following the jet mixer was made much narrower in internal diameter. The jet mixer was a 1/16" Hoke® T with an internal diameter of 0.047" and an internal length of 0.75". In these runs the organic phase was pumped straight through the 1/16" Hoke® T at 1.25 to 12.5 ml/minute using orifices from 0.01 to 0.035" in diameter. The combined aqueous KOH/$H_2O_2$ phase was pumped into the 1/16" Hoke® T at 1.78 to 17.8 ml/min via an 0.044" I.D. tube set 90° to the organic flow and using orifices 0.007 to 0.02" in diameter. In all runs here, the jet mixer and its feed lines were immersed in a 26° C. water bath. A typical run is described in detail below.

Syringe pump (3), loaded with 12.9% by weight aqueous $H_2O_2$, was started up at 0.388 ml/min. Syringe pump (2), loaded with 18.3% by weight aqueous KOH, was started up at 0.663 ml/min. Using a 27 element Kenics static mixer, the KOH and $H_2O_2$ streams were combined to a single aqueous stream flowing at 1.05 ml/min. Syringe pump (1), loaded with 5% by weight HFPO dimer acid fluoride in Freon® E2, was started up at 1.565 ml/min. Using 0.044" I.D. tubing, the combined aqueous stream was passed into the side arm of the Hoke® T at 1.05 ml/min via an orifice 0.01" in diameter. The aqueous stream then impinges into the organic stream as the organic stream flows straight through the Hoke® T at 1.565 ml/min, the organic stream having been injected into the Hoke® T via an orifice 0.02" in diameter. The ratio of reactants at this point was 4 moles of $H_2O_2$: 6.5 moles of KOH: 1 mole of HFPOCOF, making for a large excess of both $H_2O_2$ and KOH over HFPOCOF in terms of reaction stoichiometry. Fluid pressure before the jet mixer was ~30 psi and ~25 psi just after. The liquid stream was run via an 0.01" I.D. line 11" long to the product collection area. The 0.01" diameter of the exit line is such that the turbulent flow may persist after the jet mixer, although this was not confirmed by experiment. The continuous reactor was run for 20 minutes to flush out the lines and achieve steady operating conditions, this foreshot being run into waste container (7). The reactant stream was then diverted to sampling container (8) where 30 ml of organic phase were collected over 20 minutes at ambient temperature for purposes of product analysis. The organic layer was separated and washed twice with 75 ml of 5% aqueous sodium bicarbonate. The organic phase titrated 0.083 M in HFPOdP in Freon® E2 for a yield of 67.5% based on starting HFPOCOF. This yield is probably a lower limit considering that no effort was made to protect the product against thermal decomposition during the 20 minute collection period. This is Run #4 in the table below.

weight HFPO dimer acid fluoride in Freon® E2, was started up at 1.565 ml/min. The two aqueous streams were first combined in a 27 element Kenics mixer in a 3⁄16" O. D. by 7.5" length of stainless steel tubing. The combined aqueous stream was then combined with the HFPO dimer acid fluoride stream in a 1⁄8" Hoke® T fitting that emptied into a 39" long piece of 1⁄8" I.D. by 3⁄16" O.D. Teflon® PFA tubing. The ratio of reactants at this point was 4 moles of $H_2O_2$: 6.5 moles of KOH: 1 mole of HFPOCOF, making for a large excess of both $H_2O_2$ and KOH over HFPOCOF in terms of reaction stoichiometry. The Teflon® PFA tubing was passed through a focusing cavity under an ultrasonic horn delivering ~101 watts with the tip of the horn and the focusing cavity immersed in a 26° C. water bath. As the tubing passed under the horn it's contents went from clear to white and back again to two visible phases when the contents came out from under the horn. The liquid stream was run via the remaining 30" of the Teflon® PFA tubing to the product collection area. The continuous reactor was run for 20 minutes to flush out the lines and achieve steady operating conditions, this foreshot being run into waste container (7). The reactant stream was then diverted to sampling container (8) where 30 ml of organic phase were collected over 20 minutes with ice bath cooling to 0° C. for purposes of product analysis. The organic layer was separated and washed twice with 75 ml of 5% aqueous sodium bicarbonate. The organic phase titrated 0.102 M in HFPOdP in Freon® E2 for a yield of 85.3% based on starting HFPO-COF.

|     |       |       |       |       | DIMENSION IN INCHES | | | |
|     | FLOW RATES IN ML/MINUTE | | | | ORIFICES | | TRANSFER LINE | |
| RUN | COF[1] | KOH[2] | H2O2[3] | TOTAL | AQ | ORG. | LENGTH | I.D. | YIELD |
| --- | --- | --- | --- | --- | --- | --- | --- | --- | --- |
| #1 | 12.5 | 5.3 | 3.11 | 21 | 0.02 | 0.035 | 44 | 0.035 | 75.8% |
| #2 | 6.25 | 2.65 | 1.55 | 10.5 | 0.01 | 0.02 | 16.5 | 0.02 | 76.1% |
| #3 | 3.13 | 1.325 | 0.775 | 5.25 | 0.01 | 0.02 | 11 | 0.01 | 65.9% |
| #4 | 1.565 | 0.663 | 0.388 | 2.63 | 0.01 | 0.02 | 11 | 0.01 | 67.5% |
| #5 | 1.25 | 0.53 | 0.311 | 2.1 | 0.01 | 0.02 | 11 | 0.01 | 66.0% |

[1] 5% by weight HFPO dimer acid fluoride in Freon ® E2
[2] 18.3% by weight aqueous KOH
[3] 12.9% by weight aqueous $H_2O_2$ Example 64
Continuous Reactor Preparation of HFPO Dimer Peroxide in Freon® E2 Mini Ultrasonic Mixer Three ISCO pumps were used to deliver the same reactant streams as in Example 63 above to a 39 inch length of 1⁄8" I.D. by 3⁄16" O.D. Teflon® PFA tubing. A wide ultrasonic horn with tip dimensions of 1⁄4" by 3" was used to provide high intensity mixing within a 3" segment of the Teflon® PFA tubing. This was accomplished by immersing the horn in a water bath, placing a hemi-cylindrical cavity 1⁄8" under the horn, and running the Teflon® PFA tubing through the cavity. The cavity focuses the sound by reflection to increase the ultrasound intensity in the tube as it passes under the horn. This set up also avoids contact between the horn and corrosive solutions and permits larger line diameters than in Example 63. Large line diameters are particularly important if solid products such as benzoyl peroxide are to be generated.

Syringe pump (3), loaded with 12.9% by weight aqueous $H_2O_2$, was started up at 0.388 ml/min. Syringe pump (2), loaded with 18.3% by weight aqueous KOH, was started up at 0.663 ml/min. Syringe pump (1), loaded with 5% by Example 65
Continuous Reactor Preparation of HFPO Dimer Peroxide in Freon® E2 Mini Ultrasonic Mixer Continuous Phase Separation Three ISCO pumps were used to deliver the same reactant streams as in Example 63 above to a 39 inch length of 1⁄8" I.D. by 3⁄16" O.D. Teflon® PFA tubing. A wide ultrasonic horn with tip dimensions of 1⁄4" by 3" was used to provide high intensity mixing within a 3" segment of the Teflon® PFA tubing. This was accomplished by immersing the horn in a water bath, placing a hemi-cylindrical cavity 1⁄8" under the horn, and running the Teflon® PFA tubing through the cavity. The cavity focuses the sound by reflection to increase the ultrasound intensity in the tube as it passes under the horn. This set up also avoids contact between the horn and corrosive solutions and permits larger line diameters than in Example 63. Large line diameters are particularly important if solid products such as benzoyl peroxide are to be generated.

Syringe pump (3), loaded with 12.9% by weight aqueous $H_2O_2$, was started up at 0.388 ml/min. Syringe pump (2), loaded with 18.3% by weight aqueous KOH, was started up at 0.663 ml/min. Syringe pump (1), loaded with 5% by weight HFPO dimer acid fluoride in Freon® E2, was started up at 1.565 ml/min. The three streams were combined using a ⅛" union cross fitting that emptied into a 39" long piece of ⅛" I.D by 3/16" O.D. Teflon® PFA tubing. The ratio of reactants at this point was 4 moles Of $H_2O_2$: 6.5 moles of KOH: 1 mole of HFPOCOF, making for a large excess of both $H_2O_2$ and KOH over HFPOCOF in terms of reaction stoichiometry. The Teflon® PFA tubing was passed through a focusing cavity under an ultrasonic horn delivering 110 watts with the tip of the horn and the focusing cavity immersed in a 26° C. water bath. As the tubing passed under the horn its contents went from clear to white and back again to two visible phases when the contents came out from under the horn. The liquid stream was run via the remaining 30" of Teflon® PFA tubing to a glass separation vessel, from which the lower organic layer containing peroxide was pumped off at 1.5 ml/min. and sent to the product collection area. The reactor and separator were run continuously for 20 minutes to flush out the lines and achieve steady operating conditions, the separated organic phase being pumped to waste container (7). The separated organic phase was then diverted to sampling container (8) where 91 ml of the separated organic phase were collected over 60 minutes with chilling to 0° C. for purposes of product analysis. The organic layer was washed twice with 75 ml of 5% aqueous sodium bicarbonate. The organic phase titrated 0.106 M in HFPOdP in Freon® E2 for a yield of 87.4% based on starting HFPOCOF.

Example 66

Ultrasonic Batch Preparation of $[CF_3CF_2OCF(CF_3)(C=O)O]_2$

An ice chilled beaker was loaded with 3.96 g of 85% KOH pellets (0.059 mole) dissolved in 28 ml of water, 70 ml of Freon® E1, 6.13 ml of 30% aqueous hydrogen peroxide (0.060 mole), and 44 g of 33.4 wt % $CF_3CF_2OCF(CF_3)$(C=O)F (~0.052 mole) dissolved in Freon® E1. A titanium horn attached to a 40 Khz, 150 watt Dukane ultrasonic power source was immersed roughly halfway down into the pool of reactants. The ultrasonic source was turned on for 30 seconds at full power. The layers were then separated and the organic layer washed twice with 50 ml of 5% aqueous sodium bicarbonate. This gave 90 ml of 0.11 M peroxide in Freon® E1 for a 38% yield of $[CF_3CF_2OCF(CF_3)(C=O)O]_2$.

Example 67

Ultrasonic Batch Preparation of $[CF_3OCF(CF_3)(C=O)O]_2$

An ice chilled beaker was loaded with 3.96 g of 85% KOH pellets (0.059 mole) dissolved in 28 ml of water, 70 ml of Freon® E1, 6.13 ml of 30% aqueous hydrogen peroxide (0.060 mole), and 42.5 g of 26.3 wt % $CF_3OCF(CF_3)$(C=O)F (~0.048 mole) dissolved in Freon® E1. A titanium horn attached to a 40 Khz, 150 watt Dukane ultrasonic power source was immersed roughly halfway down into the pool of reactants. The ultrasonic source was turned on for 30 seconds at full power. The layers were then separated and the organic layer washed twice with 50 ml of 5% aqueous sodium bicarbonate. This gave 92 ml of 0.10 M peroxide in Freon® E1 for a 38% yield of $[CF_3OCF(CF_3)(C=O)O]_2$.

What is claimed is:

1. In a continuous process for producing acyl peroxides wherein the reaction occurs in a reaction vessel which is connected to a transfer line, comprising the steps of contacting an aqueous hydroxide and a peroxide with an acyl halide wherein the acyl halide is selected from the group consisting of R(C=O)X and RO(C=O)X in which X is —Cl, —F, —Br and —I and R is selected from the group consisting of (i) a linear or branched alkyl group of the structure $C_nF_xCl_yH_z—$, wherein x+y+z=2n+1, n is 1 to 8 and wherein the carbon bearing a —(C=O)X group is primary;

(ii) $G(CF_2)_w[CF(CF_3)CF_2]_x[OCF(CF_3)CF_2]_y[OCF(CF_3)]_z—$ where w is 0 to 8
x is 0 or 1;
y is 0 to 7;
z is 0 to 1; and
w+x+y+z≧1 and G is selected from the group consisting of —F, —COOCH₃, —SO₂F, —H, —Br, —Cl, —I, —CN, —OC₆F₅, provided that when G is —OC₆F₅ either x or w is 1; and (iii) an aromatic, hydro, chloro or perfluoro carbon compound having one or more functional groups selected from the group consisting of —F, —COOCH₃, —SO₂F, —H, —Br, —CFBrCF₂Br, —Cl, —I, —CN, —OC₆F₅;

wherein the improvement comprises combining specific reaction vessel configurations with means for supplying vigorous agitation selected from the group consisting of jet, static, ultrasonic and mechanical mixers, arranged singly or in series and wherein the agitation provided by the means for supplying vigorous agitation is at least partially maintained by flow through both the reactor and the transfer line so as to decrease reaction time to 1 minute, provided that at least 10% of the reaction occurs in the transfer line.

2. In the continuous process of claim 1 in which R is:
$G(CF_2)_w[CF(CF_3)CF_2]_x[OCF(CF_3)CF_2]_y[OCF(CF_3)]_z—$
where w is 0 to 8
x is 0 or 1;
y is 0 to 7;
z is 0 to 1; and
w+x+y+z≧1 and G is selected from the group consisting of —F, —COOCH₃, —SO₂F, —H, —Br, —Cl, —I, —CN and —OC₆F₅, provided that when G is —OC₆F₅ either x or w is 1;

wherein the improvement comprises combining specific reaction vessel configurations with means for supplying vigorous agitation selected from the group consisting of jet, static, ultrasonic and mechanical mixers, arranged singly or in series and wherein the agitation provided by the means for supplying vigorous agitation is at least partially maintained by flow through both the reactor and the transfer line so as to decrease reaction time to 0.01 to 30 seconds, provided that at least 10% of the reaction occurs in the transfer line.

3. The process of claim 1 wherein the reactor and connected transfer line are closely coupled without dead spots so as to provide continuous agitation and reaction throughout both the reactor and transfer line.

4. The process of claim 1 wherein the reaction time is 0.01 to 30 seconds.

5. The process of claim 1 wherein the peroxide is selected from the group consisting of hydrogen peroxide, alkyl hydroperoxide and metal peroxide.

6. The process of claim 5 wherein the peroxide is selected from the group consisting of $H_2O_2$ and t-BuOOH.

7. The process of claim 1 conducted within a temperature range of −10° C. to 40° C.

8. The process of claim 1 conducted within a temperature range of 0° C. to 25° C.

9. The process of claim 1 conducted at ambient temperature and without temperature control.

10. The process of claim 1 wherein X in the acyl halide R(C=O)X is —Cl or —F.

11. The process of claim 1 wherein the aqueous hydroxide is greater than 0.1 molar in water.

12. The process of claim 11 wherein the aqueous hydroxide is 1 to 5 molar.

13. The process of claim 11 wherein the aqueous hydroxide is selected from metal or tetralkyl ammonium hydroxide.

14. The process of claim 13 wherein the aqueous hydroxide is selected from the group consisting of KOH, LiOH, NaOH, CsOH and $R'_4N^+OH^-$ wherein R' is $CH_3$ or $C_2H_5$.

15. The process of claim 1 wherein the aqueous hydroxide is $R'_4N^+OH^-$ wherein R' is $CH_3CH_2CH_2CH_2$ and R is hydrocarbyl.

16. The process of claim 1 conducted in the presence of a solvent.

17. The process of claim 16 wherein the solvent is selected from a group of organic fluids characterized by their inertness toward the reactants and their ability to dissolve at least 1% of the peroxide by weight.

18. The process of claim 17 wherein the solvent is selected from the group consisting of Freon® E1, Freon® E2, Freon® 113, fluorocarbons, chlorofluorocarbons, hydrofluorocarbons, hydrofluorochlorocarbons, hexane, cyclohexane and mineral spirits.

19. The process of claim 1 conducted in the presence of a surfactant.

20. The process of claim 19 wherein the surfactant is selected from the group consisting of fluorinated surfactants and hydrocarbon surfactants.

21. The process of claim 19 wherein the surfactant is selected from the group consisting of ammonium perfluorooctanoate and sodium dodecyl sulfate.

22. In a batch process for producing acyl peroxides comprising the steps of contacting an aqueous peroxide with a peroxide and an acyl halide, wherein the acyl halide is selected from the group consisting of R(C=O)X and RO(C=O)X in which X is —Cl, —F, —Br and —I and R is selected from the group consisting of (i) a linear or branched alkyl group of the structure $C_nF_xCl_yH_z$—, wherein x+y+z=2n+1, n is 1 to 8 and wherein the carbon bearing a —(C=O)X group is primary;

(ii) $G(CF_2)_w[CF(CF_3)CF_2]_x[OCF(CF_3)CF_2]_y[OCF(CF_3)]_z$— where w is 0 to 8
x is 0 or 1;
y is 0 to 7;
z is 0 to 1; and
w+x+y+z≧1
and G is selected from the group consisting of —F, —COOCH₃, —SO₂F, —H, —Br, —Cl, —I, —CN, —OC₆F₅, provided that when G is —OC₆F₅ either x or w is 1, and (iii) an aromatic, hydro, chloro or perfluoro carbon compound having one or more functional groups selected from the group consisting of —F, —COOCH₃, —SO₂F, —H, —Br, —CFBrCF₂Br, —Cl, —I, —CN, —OC₆F₅; wherein the improvement comprises continuously agitating the reactants, using agitation means, until substantial completion of the reaction, wherein the reaction is substantially complete in less than one minute.

23. The process of claim 22 wherein the agitation means is selected from the group consisting of ultrasonic and mechanical mixers.

24. The process of claim 22 wherein the reaction time is 0.01 to 30 seconds.

25. The process of claim 22 wherein the peroxide is selected from the group consisting of hydrogen peroxide, alkyl hydroperoxide and metal peroxide.

26. The process of claim 25 wherein the peroxide is selected from the group consisting of $H_2O_2$ and t-BuOOH.

27. The process of claim 22 conducted within a temperature range of –10° C. to 40° C.

28. The process of claim 27 conducted within a temperature range of 0° C. to 25° C.

29. The process of claim 28 wherein X in the acyl halide is —Cl or —F.

30. The process of claim 22 wherein the aqueous hydroxide is greater than 0.1 molar in water.

31. The process of claim 30 wherein the aqueous hydroxide is 1 to 5 molar.

32. The process of claim 30 wherein the aqueous hydroxide is selected from metal or tetralkyl ammonium hydroxide.

33. The process of claim 1 wherein the aqueous hydroxide is selected from the group consisting of KOH, LiOH, NaOH, CsOH and $R'_4N^+OH^-$ wherein R' is $CH_3$—, $C_2H_5$— or $CH_3CH_2CH_2CH_2$—.

34. The process of claim 1 wherein the hydroxide is $R'_4N^+OH^-$ wherein R' is $CH_3CH_2CH_2CH_2$— and the acyl peroxide of the process contains no fluorine atoms.

35. The process of claim 22 conducted in the presence of a solvent.

36. The process of claim 35 wherein the solvent is selected from the group consisting of Freon® E1, Freon® E2, Freon® 113, fluorocarbons, chlorofluorocarbons, hydrofluorocarbons, hydrofluorochlorocarbons, hexane, cyclohexane and mineral spirits.

37. The process of claim 22 conducted in the presence of a surfactant.

38. The process of claim 37 wherein the surfactant is selected from the group consisting of fluorinated surfactants and hydrocarbon surfactants.

39. The process of claim 37 wherein the surfactant is selected from the group consisting of ammonium perfluorooxtanoate and sodium dodecyl sulfate.

* * * * *